United States Patent
Maki et al.

[11] Patent Number: 6,165,336
[45] Date of Patent: Dec. 26, 2000

[54] GAS SENSOR

[75] Inventors: Masao Maki, Nabari; Takashi Niwa, Ikoma-gun, both of Japan

[73] Assignee: Matsushita Electric Industrial Co. Ltd., Kadoma, Japan

[21] Appl. No.: 09/043,821

[22] PCT Filed: Sep. 27, 1996

[86] PCT No.: PCT/JP96/02802
§ 371 Date: Mar. 27, 1998
§ 102(e) Date: Mar. 27, 1998

[87] PCT Pub. No.: WO97/13147
PCT Pub. Date: Apr. 10, 1997

[30] Foreign Application Priority Data

Sep. 29, 1995 [JP] Japan .................................. 7-253200

[51] Int. Cl.[7] .................................................. G01N 27/26
[52] U.S. Cl. .................... 204/415; 204/424; 204/426; 204/429; 422/98; 427/244
[58] Field of Search ................... 204/415, 421–429; 422/98; 427/244

[56] References Cited

U.S. PATENT DOCUMENTS

| | | |
|---|---|---|
| 3,514,377 | 5/1970 | Spacil et al. .............................. 204/427 |
| 3,526,577 | 9/1970 | Molloy ...................................... 204/415 |
| 3,923,624 | 12/1975 | Beekmans et al. ...................... 204/427 |
| 3,988,233 | 10/1976 | Gamer et al. ............................ 204/415 |
| 4,088,576 | 5/1978 | Mott ......................................... 427/244 |
| 4,101,403 | 7/1978 | Kita et al. ................................ 204/429 |
| 4,304,652 | 12/1981 | Chiba et al. ............................. 204/426 |
| 4,347,732 | 9/1982 | Leary . | |
| 4,571,285 | 2/1986 | Nakazawa et al. ...................... 204/425 |
| 4,692,354 | 9/1987 | Asaeda et al. ........................... 427/244 |
| 5,082,789 | 1/1992 | Morrison et al. ........................ 422/98 |

FOREIGN PATENT DOCUMENTS

| | | |
|---|---|---|
| 0 102 067 | 3/1984 | European Pat. Off. . |
| 0 280 540 | 8/1988 | European Pat. Off. . |
| 0 299 779 | 1/1989 | European Pat. Off. . |
| 0 496 003 | 7/1992 | European Pat. Off. . |
| 43 22 143 | 9/1994 | Germany . |
| 61-172047 | 12/1986 | Japan . |

*Primary Examiner*—T. Tung
*Attorney, Agent, or Firm*—Wenderoth, Lind & Ponack, L.L.P.

[57] ABSTRACT

A gas sensor including a gas detection element and a gas selective permeation element covering at least part of the gas detection element. The gas sensor is arranged so that gases containing a gas to be detected is brought in contact with the gas detection element via the gas selective permeation element.

32 Claims, 18 Drawing Sheets

GAS SENSOR

BACKGROUND OF THE INVENTION

1. Field of the Invention

The present invention relates to a sensor for detecting combustible gas, particularly carbon monoxide contained in the general atmosphere or exhaust gas of various combustion equipment using gas and petroleum for fuel, and more particularly to a gas sensor provided with excellent characteristics with respect of stability of sensor operation under severe working environment as well as with respect of durability which raises the most serious problem in chemical sensors. However, this invention is applicable to a wide variety of chemical sensor system gas sensors used for various objects with respect to various gaseous components.

2. Description of the Prior Art

Carbon monoxide is a gas which has no color, no taste, and no scent, and is slightly lighter than air but highly toxic, and even at a concentration as low as 200 ppm, breathing the gas for 2 to 3 hours causes headaches, and at a concentration higher than 3000 ppm, death results by breathing for about 10 minutes and at 6000 ppm or higher, for a few minutes.

Because even in general home, carbon monoxide is generated by an instantaneous water heater, bath boiler, petroleum space heater, gas space heater, or charcoal fire, a carbon monoxide gas detecting sensor which can be contained in these apparatus or installed indoors, and is inexpensive, small-size, and highly reliable is strongly desired.

Examples of a gas sensor, particularly chemical sensor for detecting carbon monoxide which has been proposed to date include a type in which an electrode is mounted for absorbing and oxidizing carbon monoxide in an electrolyte and detects the carbon monoxide concentration from a current value in proportion to the carbon monoxide concentration (controlled potential electrolysis type gas sensor), in which the gas sensor is further divided into two types; one is a coulometric type in which a generated current output is to be measured and the other is a potentiometric type in which a generated voltage output is to be measured. Therefore, the coulometric type can not avoid electrolytic reaction on the electrode surfaces, resulting in deterioration of the electrode leading to an effective life shorter than that of the potentiometric type;

a type for detecting gas using a sintered compact type of an N-type semiconductor oxide, for example, stannic oxide sensitized by adding traces of metallic element such as noble metals and utilizing characteristics of these semiconductors which vary electric conductivity when in contact with combustible gas (semiconductor type gas sensor);

and a type for attaching alumina to about 20-$\mu$m platinum thin wire and heating it to a constant temperature by using a pair of reference elements with and without bearing noble metal and detecting a difference of heat generation when combustible gas comes in contact with this element to carry out catalytic oxidation reactions (contact combustion type gas sensor).

For example, there is a detailed description in "Reference 1," Chapter 14, Basics of Gas Sensors (written by Masaki Haruda) in "Sensor Practical Dictionary" in P. 112–130 supervised by Toyoaki Ohmori and published by Fuji Techno System (1986).

There also proposed a solid electrolyte type carbon monoxide sensor for detecting carbon monoxide by constituting a zirconia electrochemical cell and forming platinum/alumina catalyst layer on one side of the electrode [for example, see H. Okamoto, H. Obayashi, and T. Kudo; Solid State Ionics, 1, 319 (1980)].

The principle of this solid electrolysis type carbon monoxide sensor relies on a kind of oxygen concentration cell formed on electrodes on the catalyst layer side and naked side, in that it utilizes that at the electrode on the catalyst side, oxygen directly reaches the electrode as it is and carbon monoxide does not reach, whereas on the naked-side electrode, both oxygen and carbon monoxide reach and this carbon monoxide reduces oxygen and forms an oxygen concentration cell across both electrodes, and the electromotive force output appears.

As semiconductor type carbon monoxide sensors, in "Reference 2," Japanese Patent Publication No. Sho 53-43320 and in "Reference 3," Japanese Patent Application Laid Open No. Sho 61-50051, there proposed were methods and their improvements for detecting carbon monoxide gas by heating a gas sensor utilizing changes of resistance of a metallic oxide semiconductor in the high-temperature and low-temperature regions alternately and sampling the gas sensor output in the low-temperature region intermittently. These are characterized by the point in that the selectivity of carbon monoxide detection is improved primarily by contrivances from the viewpoint of signal processing.

In "Reference 4," Japanese Patent Application Laid Open No. Hei 1-227951, there proposed were gas sensors using as a sensor proper a metallic oxide with the resistance varied in accord with gases, in which a zeolite covered layer was provided on the surface of the sensor proper. This also aims at improving the selectivity of carbon monoxide detection.

With respect to the gas selective permeation element, ceramic gas separating membrane, that is, inorganic separating membrane has been proposed [for example, see Tatsuya Okubo and Seiji Morooka, "Current Status of Inorganic Separating Membrane and Future Development," Chemical Engineering, 12, 1 (1988, 1989)], but any proposal for applying the inorganic separating membrane to gas sensors has not yet been made to date.

All these chemical sensors have following defects. That is, controlled potential electrolysis gas sensors, semiconductor type gas sensors, and contact combustion type gas sensors basically provide characteristics for detecting hydrogen, alcohol, etc. other than carbon monoxide (CO), even if various contrivances are, in principle, made for indiscriminately reacting with reducing gas (combustible gas). That is, they have a defect in that the selectivity of CO is poor. They also have defects in that the sensor and the sensor system are, in general, expensive and the signal processing circuit of the sensor becomes complicated. Except for the contact combustion type, they have a defect of poor controllability because the sensor output to the CO concentration is nonlinear.

In particular, the biggest problem of chemical sensors which have been extensively used as gas sensors is that they cannot help becoming a fail-out detection system in spite of being a decisive sensor which involves in the safety. This is attributed to the principle in that the signal as a sensor becomes zero when no carbon monoxide is detected, and a signal is outputted when carbon monoxide is detected, and this output signal lowers as the sensor deteriorates.

To specifically describe the fail-out problem, for example, assume that using a carbon monoxide sensor, the equipment is designed under conditions to set a boundary value for the concentration of carbon monoxide and to stop the equipment when the carbon monoxide concentration exceeds this boundary value because trouble occurs from the viewpoint of safety. It is a fail-safe design philosophy to design the equipment to operate on the safety side as an equipment even if any trouble should occur, but in the case of a conventional chemical sensor system carbon monoxide sensor, there is a danger in that the sensor does not operate due to trouble caused by deterioration even though carbon monoxide is, in actuality, generated more than a certain boundary value. This is because the system is not designed to be fail-safe but fail-out, constituting a fatal problem from the viewpoint of system safety. This relates to the fact that even if a problem of disconnection of a heating means is able to be detected with respect to sensor trouble, whether the sensor itself is deteriorated or not is unable to be determined. This also relates to the shorter sensor life as compared to the equipment life.

The case in which danger of imperfect combustion increases when a gas sensor is mounted to combustion equipment for detecting imperfect combustion is more likely to occur when the combustion equipment has been used over a considerably long time, but in such event, there is a danger in which deterioration of the gas sensor has progressed, creating a problem that imperfect combustion is unable to be detected when the output signal lowers due to deterioration of the gas sensor.

Lowering, that is, deterioration, of the chemical sensor output is attributed to deterioration of electrodes or catalysts which play leading roles in the chemical sensor with time as reactions take place, and this deterioration is attributed to detection reactions of carbon monoxide being inhibited by the catalyst reduced by reducing gas such as hydrogen or hydrocarbons existing in the combustion exhaust gas or sulfur-based compounds strongly adsorbed onto the electrode surface. In these chemical sensors, noble metals are frequently used for the electrode or catalyst which plays an important role in sensor capabilities, but these noble metals are susceptible to sulfur-based compounds or silicon-based compounds and are easy to deteriorate, and has a problem of being extremely difficult to secure durability. Because the hydrocarbons coexisting in the exhaust gas of combustion equipment have large molecular weight and large molecular size, once they are adsorbed on the surface of noble metals such as platinum, etc., there are problems in that they inhibit adsorption of carbon monoxide and exert adverse effect as disturbing gas.

In addition, since the sensor system is, in principle, not designed to work on the fail safe side, a sensor with extremely high reliability in durability is required in order to put this into practical use with high reliability, but presently, there is a problem that no sensor system with a precisely established warranty in durability has been realized in the ideological level.

SUMMARY OF THE INVENTION

In view of the foregoing, it is the main object of this invention to provide a gas sensor comprising a gas detection element and a gas selective permeation element covering at least part of the gas detection element, wherein gases containing undetected gas come in contact with the gas detecting element via the gas selective permeation element.

The basic philosophy of this invention is that because a majority of sensor deterioration occurs due to coexisting gases, keeping off coexisting gases other than the gas necessary for detecting carbon monoxide from the gas detection element can achieve semipermanental durability, and if semipermanental durability can be achieved, the problem of fail-out will not have practically any meaning. That is, by configuring a gas detector in such a manner to bring gases containing undetected gas into contact with the gas detection element via the gas selective permeation element, the reach of coexisting gases to the gas detection element, which exert adverse effects on sensor life, will be restricted.

The configuration in which gases containing undetected gas comes into contact with the gas detection element via the gas selective permeation element can be achieved by the configuration comprising a base material for forming a closed space and a gas detection element equipped in the closed space of this base material, wherein part of the base material is composed by the gas selective permeation element and gases containing the undetected gas come into contact with the gas detection element via this gas selective permeation element, or by the configuration comprising a gas detection element and a gas selective permeation element for covering at least part of the gas detection element wherein the gas selective permeation element is brought in close contact with the gas detection element and gases containing the undetected gas comes in contact with the gas detection element via the gas selective permeation element.

The gas selective permeation element separates the detected gas from coexisting gases which are not required for detection by utilizing the difference of gas permeating speed in the porous body by the use of the porous body with controlled pores.

In general, the permeating mechanism of gaseous molecules in the pores of the porous body changes as follows. A stream at the gaseous phase is shifted from the viscous flow region where collision between molecules governs to the Knudsen diffusion region where collision between molecules and pore walls governs as the pore size decreases. In this event, individual properties of molecules begin to appear, and the ratio of permeation rate is theoretically given by the square root of the ratio of molecular weight. As the pore further decreases to the molecular size, the gaseous molecules lose freedom of vertical movement and are no longer able to exist as gases. This condition is called a molecular sieve. In addition, a surface diffusion coexists with a gas blow where molecules are transported while adsorbed onto the wall surfaces of pores. In particular, when pressure exceeds the capillary condensation pressure, the adsorption layer covers the whole pores, and the surface diffusion moves to the capillary condensation flow.

In the case of carbon monoxide, since the molecular weight differs from that of coexisting gases such as sulfur dioxide and hydrocarbons such as kerosene vapor, which exert adverse effects on carbon monoxide and oxygen required for operation of the gas detection element, it is possible to restrict the flow into the gas detection element at the pore size of the Knudsen diffusion region. In addition, utilizing surface diffusion, capillary condensation flow, and molecular sieves can improve the separating capability. In this invention, by forming a membrane inside the pores for controlling the pore diameter of the Angstrom order and chemically reforming surfaces inside the pores, effective permselectivity is imparted to the porous body for application.

In this event, the gas detection element is brought into contact with gas via a gas selective permeation element with the pore diameter controlled by the membrane containing one or more types of silica or zirconia. In the case of pore diameter of 10 Å or smaller, gas molecules exhibit molecular sieve type or surface diffusion type permeability and have characteristics in that the inflow is restricted by the size of gas molecules or diffusibility to the porous body inside is determined by the affinity between gas molecules and pore inner walls. The behavior of inflow and outflow of gas required for the operation of the gas detection element varies with the principle of the gas detection element, but in the case of a solid electrolysis type, carbon monoxide and oxygen flow in and come in contact with the gas detection element and carbon dioxide generated by contact reactions with oxidation catalysts flows out, but when the detection element is naked, nitrogen and steam as well as sulfur dioxide or kerosene vapor which serves as interfering gas to the detection element, and silicon-based compounds penetrate in addition to the above-mentioned gases. Since kerosene vapors or silicon-based compounds have large molecular sizes, the inflow can be effectively restricted, and that of sulfur dioxide can also be restricted in a large scale, but with respect to water vapor, since it has a molecular size of the level same as that of carbon monoxide molecule, it is, in general, unable to restrict the inflow and depending on the conditions, capillary condensation occurs within pores of the porous body, possibly blocking the pores. With this respect, it is possible to provide strong hydrophobic property by covering the surface of the gas selective permeation element with membrane containing one or more types of silica or zirconia, thereby preventing the surface diffusivity of water vapor and preventing its condensation. Similarly, it is possible to inhibit surface diffusivity of hydrophilic sulfur dioxide and block the inflow of sulfur dioxide. With the above configuration, poisoning effects on the elements constituting the gas detection element such as oxide catalysts, platinum electrodes, etc. can be alleviated. It is preferable to use ceramics for the base material of porous body from the viewpoint of heat resistance.

For the gas detection element of this invention, any of the dry chemical sensor elements, for example, contact combustion type, semiconductor type, or solid electrolysis type can be used.

For heat sources necessary for driving gas detection elements, if the working environment is already in the operable temperature, no heat source is required, but heating of the gas detection element equipped to a gas sensor is designed to be achieved by a heating means, and temperature control is carried out as required by using simultaneously a temperature detecting means such as a thermister, thermocouples, etc. For the heating means, various means such as heating wire, resistance heating membrane, etc. can be applied, and for the material used for resistance heating membrane, noble metals such as platinum are preferable in terms of durability, and if heating wire is used, iron-chromium system and nickel-chromium system can be used.

Now description will be made as follows on the ceramic porous base material which serves as a base of gas selective permeation element. The ceramic porous base material is fabricated by using commercially available porous ceramics or porous glass. Porous ceramics and porous glass are used in various applications as ceramic filters, and for example, their application to separation of beer yeast is well known. The pore size ranges from 0.05 μm to several μm, but because the gas selective permeability is unable to be obtained as it is, the pores must be filled up to control the pore size.

For a control method of pore size, a method for forming sol-gel membrane on the pore surface or a CVD method for controlling the pore by forming membrane inside the pore by pyrolysis are effective, but various membrane forming methods which have been known to date are applicable. Of these, for example, methods for utilizing decomposition reaction of metal-alkoxide (sol-gel method) or CVD reaction are effective and it is possible to control the pore size up to the pore size of the molecular diffusion region. By these methods, the pore size can be controlled to uniform pore sizes of 10 Å or less in mean pore size. The CVD method can control the pore size more accurately and uniformly than the sol-gel method. The size of pore in this event must achieve the size of gas molecules, and transition of gas inside the pore of porous body, in actuality, provides complicated diffusion characteristics with effects of interaction between the substance on the pore surface and gas added, but basically, the gas permeating process is included in the region of molecular sieve diffusion or surface diffusion, and it becomes necessary to prevent large-size molecules or molecules with little affinity to pore inner walls from passing the gas selective permeation element by providing characteristics for markedly inhibit permeation of large-size molecules or for allowing the diffusion characteristics to be regulated by the affinity to fine-pore inner walls.

For the shape of ceramic porous bodies, various shapes such as tubular, sac, or disc can be applicable. It is also allowed to combine non-permeable heat-resistant base material such as ceramics or metal and use gas selective permeation element for part of the non-permeable base material.

It is also possible to use gas detection elements of various shapes in combination with gas selective permeation elements of various shapes. The two shall be arranged in such a manner that the element is enclosed in or in close contact with the gas selective permeation element. For example, if the profile of the gas selective permeation element is tubular or sac, it is practically advantageous to use the gas detection element housed inside the porous body. In the case of a disc form, the gas detection element shall be brought in close contact with the surface of the disc-form gas selective permeation element for integration.

Now, because when a tubular gas selective permeation element is used, the gas detection element is arranged from the gas selective permeation element via a space, if there is any defect (large pore) in pores of the porous body, inhibiting gas enters through this pore, possibly degrading the gas detection element. However, in the case of tubular porous body, the CVD method is easy to apply and it becomes advantageous for forming a porous body of uniform pore sizes. That is, in the case of cylindrical porous body, because it is possible to feed a membrane forming material for blocking pores into pores together with carrier gas, thermally decompose while continuously permeating, and carry out pore control, membrane forming process of pores preferentially takes place with pores with large permeability, and therefore, it is possible to fabricate a gas selective permeation element with uniform pore size distribution, thereby dissolving the above-mentioned fears.

On the other hand, when disc type gas selective permeation element is used, since the gas detection element is used by bringing it into close contact with the surface of the disc type gas selective permeation element for integration, for example, in the case of the solid electrolysis system, electrodes are formed in close contact with the porous body, even if the pore size is nonuniform and defects (large pores) are included, the electrode at the portion may be poisoned and deteriorated by poisoning gas but the electrode portion in contact with normal pores is protected and is able to avoid deterioration. The effects when the oxidation catalyst is carried inside the pores of the porous body are the same as those described as above, and the catalyst formed inside the pores of normal size are not subject to deterioration of poisoning gas and can achieve long life of the gas sensor.

Next discussion will be made on the operation of the gas sensor according to this invention. That is, gas contained in general atmosphere or exhaust gas of the combustion equipment first comes in contact with the pores of the gas selective permeation element but gas with larger molecular size than the pore size, such as kerosene vapor or silicon oligomer is unable to penetrate the sensor inside or is remarkably restricted of its penetration. Reactive gases such as $SO_2$ or $NO_2$ are difficult to diffuse into pores because of large molecular weight and poor affinity to pore walls and are scarcely able to reach the gas detection portion. Gas molecules of low molecular weight such as oxygen, carbon monoxide, nitrogen, etc. can freely reach the gas detection portion under the condition close to Knudsen diffusion. Water vapor does not undergo capillary condensation inside pores due to poor affinity to pore walls, and consequently, pores are not blocked. With the above configuration, deterioration of the element which fulfills main functions of the gas detection element such as platinum electrode or oxidation catalyst can be prevented and extended life of the gas sensor can be expected.

By using the configuration in which gases containing undetected gas come in contact with the gas detection element via the gas selective permeation element, in general, there causes a fear in which responsibility is impaired or sensitivity lowers as compared to the case in which the gas detection element is independently used. The gas sensor according to this invention hardly affects the responsibility. This is natural behavior because the gas selective permeation element does not interfere with permeation of carbon monoxide, detected gas. With respect to the sensitivity, the characteristics vary with the principle of the gas sensor, and in the case of solid electrolyte element, a slight drop of sensor output is recognized. However, this is the level which does not cause any practical hindrance. In the case of semiconductor element, the sensitivity does not lower. In the semiconductor system, generally restricting the inflow of reducing gas allows the characteristics to shift slightly to the high-temperature side and the carbon monoxide-resistance characteristics to generally shift in parallel. Because the temperature dependency changes to the diffusion-dominant type, the characteristics are stabilized.

DETAILED DESCRIPTION OF THE INVENTION

Figure 1:
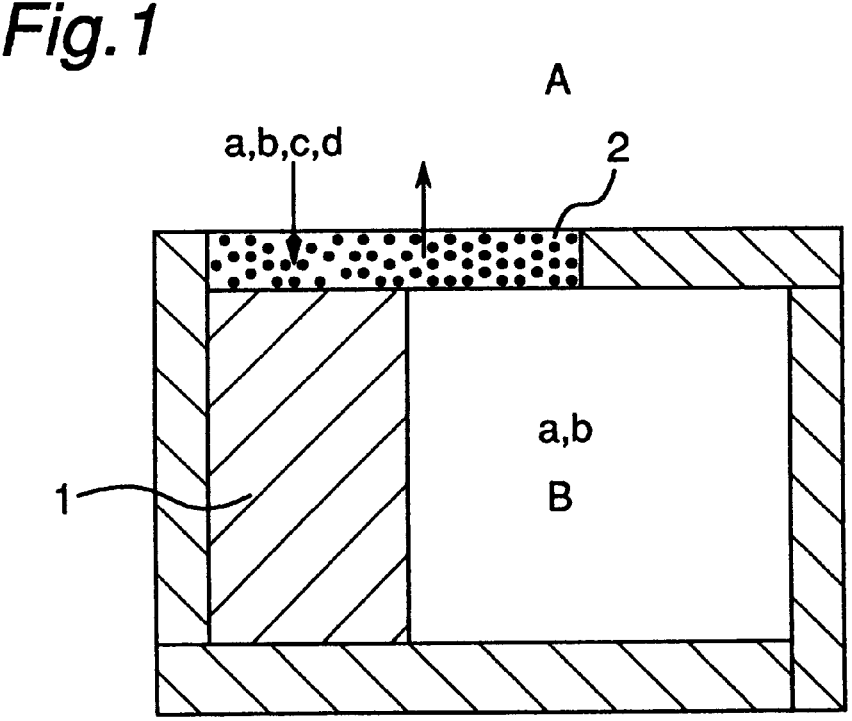
FIG. 1 is a cross-sectional view showing a gas sensor related to a first embodiment according to the present invention.

The first embodiment according to this invention comprises a gas detection element and a gas selective permeation element covering at least a part of the gas detection element, wherein gases containing a gas to be detected come in contact with the gas detection element via the gas selective permeation element. By the gas selective permeation element, a gas to be detected is separated from other gases and as a consequence that a gas to be detected alone or preferentially a gas to be detected is fed to the gas detection element, stable operation as a gas sensor and long-time durability are secured. That is, because the gas detection element comes in contact with a gas to be detected via the gas selective permeation element, gases which deteriorate the elements that play an important role in the functions of the gas detector (for example, oxidation catalyst in the case of contact combustion system, N-type semiconductor oxide membrane in the case of semiconductor system, electrode and porous oxidation catalyst membrane in the case of solid electrolyte system, etc.) have their inflow restricted or blocked to prevent deterioration of the gas detector. With this configuration, unstability, always the biggest drawback of the chemical sensor, that is, problems associated with durability such as great displacement of the zero point with time or lowered sensor outputs due to deterioration of the element which fulfills main functions of the gas detection element can be solved.

The second embodiment according to this invention covers an arrangement embodying the first embodiment, comprising a base material forming a closed space and a gas detection element mounted in the closed space of this base material, wherein at least a part of the said base material is composed with the gas selective permeation element and gases containing a gas to be detected are designed to come into contact with the gas detection element via this gas selective permeation element. This composes a gas sensor by forming at least a part of the base material so as to constitute a closed space for housing the gas detection element inside this closed space with respect to the arrangement of the gas detection element and gas selective permeation element. With the gas selective permeation element, a gas to be detected is separated from other gases, and a gas to be detected alone or preferentially a gas to be detected is fed to the gas detection element, and as a result, stable operation as a gas sensor and long-time durability can be secured. This system is available in various combinations of gas selective permeation element and base material as well as profiles, but it is also available in various combinations with various profiles of gas detection elements. Effects related to durability and operation stability are similar to those of the first embodiment.

The third embodiment according to this invention covers an arrangement embodying the first embodiment, comprising a gas detection element and a gas selective permeation element which covers at least a part of the gas detection element, wherein the gas selective permeation element comes in close contact with the gas detection element and gases containing a gas to be detected are designed to come into contact with the said gas detection element via the gas selective permeation element. Also, gas a' generated by contact reactions with the catalysts flow out of the gas selective permeation element. In the case of this embodiment, if pores of the gas selective permeation element should be imperfect, in the case of the second embodiment, interfering gas with large molecular size flows in through the defective large size pore, possibly extending deterioration to the whole gas detection element, whereas in the case of this embodiment, even if interfering gas with large molecular size flows in, the portion of the gas detection element in close contact with the pore may locally be deteriorated, but for the majority of pores free of trouble, effects persist and a gas sensor with high level of practical reliability can be achieved.

The fourth embodiment according to this invention comprises further adding a heating means for heating the gas detection element in embodiments 1 to 4. Depending on the type of the gas detection element and the installation environment of the gas sensor, a large number of gas detection elements require a heating means for the operation. The basic operation and effects of this embodiment are similar to those mentioned above.

The fifth embodiment according to this invention uses a gas selective permeation element with pore sizes controlled to 3–100 Å in particular for the gas selective permeation element in embodiments 1 to 4. The gas selective permeation element with pore sizes controlled to 3–100 Å exhibits the following actions. That is, gases containing undetected gases first diffuse into pores with pore sizes controlled to 3–100 Å but gases with larger molecular sizes than pore sizes, for example, kerosene vapor or silicon oligomer is not able to penetrate into the sensor inside. Because the reactive gases such as $SO_2$ or $NO_2$ have large molecular weight, they are hard to diffuse inside pores and the amount reaching the gas detection portion decreases. The gas molecules of low molecular weight such as oxygen, carbon monoxide, nitrogen, etc. can freely reach the gas detection portion under the condition close to Knudsen diffusion. The size of pore diameter is extremely important and gas selective permeability remarkably lowers when the pore diameter exceeds 100 Å. It is preferable to achieve 3–100 Å pore sizes in order to allow the gas selective permeation element to exhibit gas selective permeability. In this event, gas diffusion reaches the region of molecular sieves and perfect selective permeability can be obtained. In the case of pore sizes from 10 Å up to 100 Å, because the gas diffusion becomes the Knudsen diffusion region and large-size molecules have effects of restricting the inflow, prevention of deterioration of electrodes or catalyst and contribution to extended life can be expected. When the gas selective permeation element and electrode are separated via a space, uniformity of pore size is particularly important, and an existence of even one pore in the membrane may impair the selectivity. However, when the electrode involved in gas adsorption is in close contact with the ceramic gas selective permeation element, directly, effects similar to those of the configuration with the electrode split by pores are obtained, and even if a large pore is mixed, the electrode in the very portion deteriorates but the electrodes in contact with small pores of other sizes are protected by gas selective permeability and deterioration can be avoided. For the uniformity of sizes of pore diameter, if the condition is such that 3–100 Å account for 50%, which can provide molecular sieve effects, favorable effects can be expected in the region where other pores are 100 Å or less and are in the Knudsen diffusion region.

The sixth embodiment according to this invention uses an alumina compounds or a zirconia compounds, in particular, for the base material of the gas selective permeation element in embodiments 1 to 5. This is used to improve reliability of the gas sensor with respect repeated expansion and shrinkage by matching the thermal expansion coefficient of the gas selective permeation element to that of the gas detection element as much as possible, in particular, in the combination with high-temperature operating elements such as solid electrolyte system when the gas detection element is used in combination with the gas selective permeation element. It is so configured from viewpoint of improvement of the overall reliability as a gas sensor while chemical deterioration of the gas detection element is prevented and service life is extended in the basic configuration of this invention.

The seventh embodiment according to this invention uses the gas selective permeation element, in particular, with its surface covered with zirconia, silica, or their mixture in embodiments 1 to 6. This is particularly intended to block hydrophilic gas such as water vapor or sulfur dioxide which has a fear of affecting molecular sieve effects of the gas selective permeation element by hydrophobic-treating the surface of the gas selective permeation element. Because the gas detection element comes in contact with the detected gas through the gas selective permeation element with the pore surface covered with a membrane containing one or more kinds of silica or zirconia, deterioration of the gas detection element can be prevented by restricting or blocking the entry of the gas deteriorating the element which fulfill main functions of the gas detection element (for example, oxidation catalyst in the case of contact combustion type, N type semiconductor oxide membrane in the case of semiconductor system, and electrode and porous oxidation catalyst membrane, etc.). And, in particular, the gas selective permeation element with the mean pore diameter controlled to 10 Å or less tends to cause fear of blocking pores by capillary-condensing water vapor in pores, but since the pore surface of the gas selective permeation element is treated with the membrane containing one or more kinds of silica or zirconia which provide strong hydrophobicity, it does not capillary-condense water vapor in pores, enabling the stable long-time operation. The unstability, the biggest drawback of chemical sensors for a long time, that is, the problem involved in durability in which the zero point greasy shifts with time and the sensor output lowers due to deterioration of the elements which fulfill the main functions of gas detection element can be resolved.

The eighth embodiment according to this invention uses a solid electrolyte element comprising an oxygen ion conductor and a pair of electrodes and a porous catalyst membrane as a gas detection element in embodiments 1 to 7.

That is, for an oxygen ion conductor, fluorite type solid solution of zirconia system such as $ZrO_2$-$Y_2O_3$ (yttria stabilized zirconia) or $ZrO_2$-$CaO$ (carcia stabilized zirconia), etc. or ceria system such as $CeO_2$-$Sm_2O_3$, or $Bi_2O_3$ base composite oxides with $Y_2O_3$, $Gd_2O_3$, $Nb_2O_5$, $CaO$ dissolved in $Bi_2O_3$, or mixed conduction with electronic conduction is used, but rare earth —transition metal system perovskite compounds such as the $CeO_2$ base or $Ce_{0.9}Ca_{0.1}O_{1.9}$ or $La_{1-x}Sr_2CoO_3$ can be used.

For the purpose to form a solid electrolyte element, the oxygen ion conductor is excellent from the viewpoint of stability, but it is possible to use fluoride ion conductor or proton conductor other than oxygen ion conductor by forming their moldings of various shapes or membranes on the substrate. In the electrochemical cell in which a pair of electrodes are formed on the surface using solid electrolyte, if the oxygen concentration differs between electrodes, an oxygen concentration cell is formed and electromotive force is generated and a concentration cell type oxygen sensor element can be constituted. In addition, in a porous catalyst membrane in which one of the electrodes is covered with porous oxide catalyst, the following chemical reaction takes place $$CO+1/2O_2 \rightarrow CO_2 \qquad (1)$$

and strictly speaking, it varies with the gas diffusion rate and the catalyst oxidation reaction rate, but the concentration of carbon monoxide reaching the electrode surface decreases. On the electrode on the side of the porous oxidation catalyst membrane provided, oxygen is exclusively adsorbed, whereas on the side of the naked electrode free of catalyst, carbon monoxide and oxygen are adsorbed. The oxygen adsorbed at electrodes and the oxygen ion of solid electrolyte attain the equilibrium state, but the oxygen ion inside the solid electrolyte on the side of naked electrode free of catalyst is reduced by carbon monoxide adsorbed to the electrode, generating imbalance of oxygen ion concentration between two electrodes. Here, a difference of chemical potential is generated between both electrodes and an oxygen concentration cell is formed and electromotive force is obtained. In the atmosphere or even under exhaust gas conditions of combustion equipment, the oxygen concentration exists more than several percents at minimum, whereas carbon monoxide must be detected at 2000 ppm or less, at maximum, and since oxygen is ½ mol as against 1 mol of carbon monoxide as given in Eq. (1), the difference of oxygen concentration on the electrode surface when it is evaluated in bulk is small and the influence of carbon monoxide concentration is exclusively dominant in the electromotive force. As a result, the carbon monoxide concentration increases and output increases. That is, this works as a carbon monoxide detection sensor. This sensor basically relates to the catalyst characteristics, but as long as gas is combustible gas, not to mention carbon monoxide, detection takes place with varying sensitivities. For example, hydrogen gas indicates large sensor outputs.

The porous oxidation catalyst comprises porous membrane containing active oxidation catalyst particles with continuous permeability, and the membrane can be formed by a wet process in which pastes containing oxidation catalyst particles, porous material, binding agent, etc. are applied and fired or a dry process using plasma spraying. In addition, the catalyst may be dispersed in the ceramic foams or ceramic fiber cloth or nonwoven cloth with continuous permeability or carried on their surfaces.

For the oxidation catalyst, there used are catalyst particles comprising compound oxides or mixture having a spinner structure such as $CuCo_2O_4$ containing transition metals such as Mo, Cu, Ni, Co, Fe, etc. or perovskite structure such as $LaCoO_3$ or particles with noble metal elements such as Pt, Pd, Rh, etc. carried on the thermal-resistant metal oxide carrier on fine particles such as alumina.

The solid electrolyte may be used as a bulk body of flat, disc, tubular shapes as sintered ceramic formed products or may be used by forming membrane using a dry process such as sputtering, laser ablation, or plasma spraying as well as a wet process such as sol-gel process. If it is used for a bulk body, since impedance is large, there is a case in which it is advantageous to use in the form of membrane intended for low-temperature operation. The solid electrolyte element deteriorates the electrode when used as naked, but in this configuration, the intrusion into the gas detection element of poisoning gas that deteriorates electrodes is blocked, a gas sensor with remarkably long life can be obtained.

The ninth embodiment according to this invention is a solid electrolyte element comprising an oxygen ion conductor and a pair of electrodes in embodiments 1 to 7 and is used with a catalyst carried in pores in a part of the gas selective permeation element. In place of the porous catalyst membrane which is used in the eighth embodiment, it is used with the catalyst carried in pores of part of the region of gas selective permeation element. Because the catalyst is formed inside pores, no catalyst membrane is required and a small-size gas sensor can be realized. The operation as a gas detection element is the same as that described above, and effects with respect to the life are same.

The tenth embodiment according to this invention uses a semiconductor element containing N-type semiconductor oxide composite as a gas detection element in embodiments 1 to 7. Description is made on the semiconductor element. For example, comb type metallic electrodes are formed on the insulation substrate such as alumina. For the electrode forming method, in practice, inexpensive thick-film printing method is preferable. When the form is cylindrical, curved surface printing shall be carried out or the electrode shall be transferred using transfer paper. Gold or platinum electrodes are desirable for electrode material from viewpoint of stability. On this electrode, composite membrane primarily composed with N-type semiconductor oxides such as stannic oxide, indium oxide, zinc oxide, etc. is formed. The membrane containing these N type semiconductor oxides traps oxygen and provides high resistance under heating conditions, but this membrane provides characteristics in that oxygen is taken away and the trap is canceled when it comes in contact with the reducing gas such as carbon monoxide, and the resistance lowers, thereby enabling gas detection. The semiconductor used as naked causes the N-type semiconductor oxide composite to adsorb poisoning gas such as sulfur dioxide and deteriorates, but since it is protected by the gas selective permeation element, long life is guaranteed.

The eleventh embodiment according to this invention comprises a pair of gas selective permeation element in embodiments 1 to 7, allows one side of gas selective permeation element to carry an oxide catalyst, laminates a heating membrane on one side of the other gas selective permeation element and electrode membrane, oxygen ion conductive solid electrolyte membrane, and another electrode membrane in turn on the opposite side surface, and oppositely arranges and seals membranes on both sides. The temperature required for operation of the gas detection element is realized by the heating membrane mounted to the gas selective permeation element. With respect to the electrodes arranged on both surfaces of oxygen ion conductive solid electrolyte membrane, to one electrode, carbon monoxide is oxidized by passing the gas selective permeation element with the oxidation catalyst carried, the interfering gas of high molecular weight is eliminated, gas which does not contain carbon monoxide but contains oxygen reaches, while to the other electrode, interfering gas of high molecular weight is removed and gas containing both carbon monoxide and oxygen reach. Consequently, an oxygen concentration cell is formed across electrodes and gas detection is enabled. Effects as a gas selective permeation element are same as those of the above-mentioned embodiments.

The twelfth embodiment according to this invention comprises carrying the oxidation catalyst in pores of part of the region of the gas selective permeation element, in embodiments 1 to 7 forming electrodes, respectively, in the region with the oxidation catalyst carried and the region not carried, and laminating oxygen ion conductor layers, ceramic insulator layer, and heating coated layer in turn on this pair of electrode. In place of using a pair of gas selective permeation element in the eleventh embodiment, the oxidation catalyst is carried in the pore of part of the region, and similar functions are fulfilled. Operation, etc. are same as those described above.

The thirteenth embodiment according to this comprises a pair of flat plate type gas selective permeation element in embodiments 1 to 7, equips heating membrane on one side of gas selective permeation element, on the rear surface side, laminates electrode membrane, oxygen ion conductive solid electrolyte membrane, another electrode membrane, and porous catalyst membrane in turn, above which the other selective permeation element oppositely arranges and seals membranes on both sides. This gas sensor can combine the solid electrolyte element with the flat plate type gas selective permeation element under the completed condition, having characteristics in fabrication. Effects as a gas selective permeation element are same as those of the above-mentioned embodiments.

The fourteenth embodiment according to this invention arranges oppositely ceramic insulation plates equipped with plate type gas selective permeation element with heating membrane equipped on one surface, oxygen ion conductive solid electrolyte membrane, a pair of electrodes, and porous catalyst layer equipped on the other electrode, and seals. In the thirteenth embodiment, the electrode films and oxygen ion conductive solid electrolyte membrane are sandwiched, whereas in this embodiment, electrode membrane are designed to have on the same surface side. The operation and effects, etc. in terms of durability as gas sensor are same as those described above.

The fifteenth embodiment according to this invention relates to the manufacturing method of the gas sensor, comprising a process for carrying platinum group element in pores of one of a pair of gas selective permeation element, a process for forming in turn a platinum electrode, oxygen ion conductive solid electrolyte membrane, and platinum electrode by sputtering in a specified pattern using a masking jig, and further after a process for joining external lead wires from the platinum electrodes, a process for joining the periphery of the other flat plate type gas selective permeation element with a resistance heating membrane formed on its rear surface. For the gas selective permeation element, ceramic porous body used as a base material and fabricated with pores controlled by the sol-gel process or CVD process is used. The catalyst bearers of the gas selective permeation element is fabricated by drying and sintering after immersing in a salt aqueous solution containing platinum group elements. Use these as base material and form membranes of main functional elements of the gas sensor by sputtering. Carrying out multi-layer sputtering for electrode membranes and oxygen ion conductive solid electrolyte membranes will become advantageous from viewpoint of process. Because the membrane is formed in a batch but downsizing masking patterns can fabricate a large number of elements in one operation and elements car be fabricated in small sizes, there is no drawback as a batch from the viewpoint of productivity. From this process, gas sensors with stable characteristics can be obtained.

The sixteenth embodiment according to the present invention relates to the manufacturing method of gas sensors, comprising a process of carrying platinum group elements in part of the region of pore of gas selective permeation element, a process of forming platinum electrodes, oxygen ion conductive solid electrolyte membrane, an insulator membrane by sputtering in specified patterns using masking jigs, and then, a process for joining from platinum electrodes and forming resistance heater membrane on the insulator membrane. By this method, the sputtering process is required only once for the platinum electrodes, and as compared to the process described before, it becomes advantageous from viewpoint of costs. The process conditions are same as those of the fifteenth embodiment.

The seventeenth embodiment according to the present invention has a pair of electrode membranes on both surfaces and an oxygen ion conductor with porous oxidation catalyst layer on one of the electrodes housed in a cylindrical gas selective permeation element for either of the gas sensors of embodiments 1 to 7, and provides a heating means on the circumferential portion. The heat source required for operation of the solid electrolyte element is secured with a heating means of the outer periphery portion. Because the tubular gas selective permeation element is strong against thermal shock depending on its profile, and a CVD process can be applied for a method for fabricating the gas selective permeation element, a gas selective permeation element with uniform pore sizes can be obtained. Since the CVD method can form membranes while allowing gas for controlling pores to flow in pores, treatment gas flows preferentially from pores of larger sizes and control of pores takes place. The oxidation catalyst membrane of the solid electrolyte element and electrodes are porous bodies and are protected from poisoning and deterioration in the same manner as described before. The operation of the solid electrolyte element depends on the ratio of the oxygen concentration adsorbed to a pair of electrodes formed on the solid electrolyte bases, and therefore, even if part of the porous body surface is blocked with foreign matter, the characteristics are free of any influence and high stability is secured. Storing them in the tubular gas selective permeation element lowers outputs by the solid electrolyte elements but does not affect operations at all as well as other characteristics such as responsibility.

The eighteenth embodiment according to this invention houses a plate type oxygen ion conductor comprising a pair of electrode film on one surface and a porous oxidation catalyst layer on one electrode in either of the gas sensors of embodiments 1 to 7 in a tubular gas selective permeation element and provides a heating means around its circumferential portion. In the previous embodiment, the electrodes are arranged on opposite sides via the plate type oxygen ion conductor, whereas in this embodiment, electrodes are provided on the same side. Operation and characteristics of this sensor are same as those described before.

The nineteenth embodiment according to this invention has a pair of electrode membranes on one side in either of the gas sensors of embodiments 1 to 7, and joins the surface with no electrode formed of the plate type oxygen ion conductor with the porous oxidation catalyst layer formed on one electrode with non heater membrane surface of the insulator plate with a heater membrane and houses this joined plate type oxygen ion conductor and the insulation plate inside the tubular gas selective permeation element. In the previous embodiments, the heating means are provided on the circumferential portion, whereas in this embodiment, the heater membrane is provided on the insulator plate to use it for heat sources for the solid electrolyte element. The operation and characteristics of the gas sensor are same as those described above.

The twentieth embodiment according to this invention has a pair of electrode membranes on outer surface in either one of the gas sensors according to embodiments 1 to 7, has a porous oxidation catalyst layer on one of the electrodes and houses the tubular oxygen ion conductor with heater wire in the tubular gas selective permeation element. The tubular oxygen ion conductor is fabricated by sintering the formings produced by press, extrusion, or injection molds. The electrode membranes fabricated by local printing are used. The heat source required for operation of the solid electrolyte element is provided by heater wires arranged inside the tubular oxygen ion conductor. The operation and characteristics of the gas sensor are same as those described above.

The 21st embodiment according to this invention uses ceramic paper with oxidation catalyst particles mixed in ceramic fibers as a porous oxidation catalyst layer in either of the gas sensors according to embodiments 17 to 20. This ceramic paper is fabricated by papermaking, pressing, and drying the oxidation catalyst particles dispersed together with silica alumina fibers and the binding agent such as glass or inorganic adhesives. Because oxidation catalyst particles are dispersed satisfactorily in the ceramic fibers, the permeability of gases such as oxygen is good and a porous oxidation catalyst layer with extremely excellent oxidation catalyst capabilities can be obtained. The operation and characteristics of the gas sensor are same as those described above.

The 22nd embodiment according to this invention forms non-oxidized porous layer on the electrode free of porous oxidation catalyst layer in either of the gas sensors according to embodiments 17 to 20. With the non-oxidized porous layer, the balance of oxygen diffusibility is achieved with the porous oxidation catalyst layer and at the same time, the reach of poisoning molecule to the electrode is inhibited to secure longer life of the electrode. When a gas selective permeation element in the Knudsen diffusion region is used for the gas selective permeation element, the gas molecule with large molecular weight is restricted of its inflow but is not perfectly blocked. In such case, effects for protecting electrodes are exhibited.

The 23rd embodiment according to this invention uses the material with the non-oxidized porous layer comprising primarily zirconia or silica in the 22nd embodiment. This intends for avoiding influence of particularly sulfur dioxide by the use of hydrophobic materials. The operation and characteristics of the gas sensor are same as those described above.

The 24th embodiment according to this invention seals by joining the plate type gas selective permeation element to the electrode surface side of the substrate having a pair of interdigital electrodes on one surface of the insulated substrate and in addition, an N type semiconductor oxide system sintered membrane on the electrode and a heater membrane on the other surface. This embodiment joins and seals the semiconductor element with an interdigital electrode formed on one side of the substrate and further an N-type semiconductor oxide system sinter membrane formed on the same surface as well as the electrode heater membrane formed on the other surface with the plate-type gas selective permeation element in order to protect the surfaces on which electrodes of the semiconductor element and N-type semiconductor oxide system sinter film are formed.

The heat required for operation of the semiconductor element is obtained by the heater membrane. The operation and characteristics of the gas sensor are same as those described above.

The 25th embodiment according to this invention relates to the manufacturing method of semiconductor type gas sensor of this invention, comprising a process for forming a pair of interdigital electrode on the other surface of the insulating substrate with the heater substrate formed on one surface, and a process for patterning and applying glass-base or inorganic adhesive base pastes to circumferential surfaces on the electrode surface side of the element fabricated by the process for applying and sintering the paste containing N-type semiconductor oxide on the electrode, and at the same time a process for joining and sintering the plate type gas selective permeation element patterned and applied with pastes. Because all the basic processes use the thick membrane printing process by screen printing, the outstanding productivity of elements is achieved and gas sensors can be fabricated at comparatively low prices. Pastes for printing are prepared by dispersing and compounding material components primarily comprising N-type semiconductor oxides with solvents, binding agents, and stabilizers by the use of automatic mortar or triple roll mill.

The 26th embodiment according to this invention houses in the tubular gas selective permeation element the gas detection element with a pair of interdigital electrode membranes formed on the outer surface of the tubular insulation substrate in embodiments 1 to 7, N-type semiconductor oxide base coating layer laminated on this electrode membrane, and at the same time with heater wire arranged inside the tube. The tubular gas selective permeation element is formed in the same manner as is the case of the 17th embodiment. A pair of comb-type electrode membrane is directly formed on the outer surface of the tubular insulation substrate by thick membrane printing method by local printing, etc. or by transferring the membranes formed by various methods. The N type semiconductor oxide system coated layer on this electrode membrane is also formed by the thick membrane printing method. The heat required for operation of the semiconductor element is provided by the heater wire inside the tube. The operation and characteristics of the gas sensor are same as those described above.

The 27th embodiment according to this invention houses in the tubular gas selective permeation element the gas detection element with a pair of interdigital electrode membranes formed on one surface of the plate-form insulation substrate in embodiments 1 to 7, N-type semiconductor oxide base coating layer laminated on the electrode, and with heater wire on the other surface. The operation and characteristics of the gas sensor are same as those described above.

The 28th embodiment according to this invention houses in the tubular ceramic gas selective permeation element the gas detection element with two pairs of interdigital electrode membranes formed on both surfaces of the plate-form insulation substrate in embodiments 1 to 7, N-type semiconductor oxide base sinter layer on the electrodes of relevant surfaces, and a porous carbon monoxide catalyst layer on one N type semiconductor oxide base coated layer and porous selective hydrogen oxidizing catalyst layer without oxidizing capability of carbon monoxide but with hydrogen oxidizing capability on the other. In order to stabilize the characteristics of the semiconductor system gas detection element, the elements for detecting carbon monoxide and for detecting gases excluding carbon monoxide are housed inside a tubular ceramic gas selective permeation element equipped with heating means on the outer circumference. By the effects of the gas selective permeation element, life as a gas sensor can be extended. Two sensor outputs as semiconductor system can be obtained, but by processing these outputs, noise influence, etc. can be canceled, resulting in high reliability as a gas sensor.

The 29th embodiment according to this invention houses in a tubular gas selective permeation element a gas detection element comprising an N type semiconductor oxide system coated layer provided on the surface of the element configured with the heater coil and the lead wire in embodiments 1 to 7. The N type semiconductor oxide system coated layer is heated by energizing the heater coil. From the lead wire, resistance changes of the N type semiconductor oxide base coated layer are taken out. Since the semiconductor system gas detection element itself can be made into an extremely small-size element in this configuration, there is an advantage in that the whole gas sensor can be made into a small-size low-consumption type. The operation and characteristics of the gas sensor are same as those described above.

The thirtieth embodiment according to this invention uses a porous substrate for the insulation substrate in embodiments 26, 27, and 28. The use of the porous substrate makes the N type semiconductor oxide base coated layer porous, achieving an effect of improved detection sensitivity of carbon monoxide. The operation and characteristics of the gas sensor are same as those described above.

The 31st embodiment according to this invention is to make the N type semiconductor oxide base coated layer a laminated membrane comprising the first coated layer containing indium oxide and the second coated layer containing noble metal or P type semiconductor oxide sensitizer in embodiments 26 to 29. The first coated layer containing indium oxide is a membrane of N type semiconductor oxide system, which carries out detection operation by lowering the resistance with respect to carbon monoxide, but laminating the second coated layer containing noble metal or P type semiconductor oxide sensitizer on the first coated layer further increases the sensitivity. These noble metals or P type semiconductor oxide sensitizers, for example, adsorb, condense, and spill over carbon monoxide, feeds carbon monoxide to the membrane of the N type semiconductor oxide system, or provides quantum effects to the N type semiconductor oxide to increase the density of conductive carrier for sensitization. The operation and characteristics of the gas sensor are same as those described above.

The 32nd embodiment according to this invention is to make the N type semiconductor oxide base coated layer a laminated membrane comprising the first coated layer containing stannic oxide and the second coated layer containing noble metal or P type semiconductor oxide sensitizer in embodiments 26 to 29. The first coated layer containing stannic oxide is a membrane of N type semiconductor oxide system, which carries out detection operation by lowering the resistance with respect to carbon monoxide, but laminating the second coated layer containing noble metal or P type semiconductor oxide sensitizer on the first coated layer further increases the sensitivity. Compared to the former embodiment, this embodiment has a characteristic of high sensitivity on the low-temperature side. Conversely, temperature characteristics become larger for this embodiment. Compared to the former embodiment, the effective sensitizer differs. In the case of this configuration, sensitization effects particularly of palladium are outstanding.

The 33rd embodiment according to this invention configures the N type semiconductor oxide base coated layer with a coated layer containing indium oxide and $CuFe_2O_4$ and gold in embodiments 26 to 29. Compared with the 31st and 32nd embodiments which are 2-coat types, respectively, and are difficult to control combinations such as membrane thickness, this embodiment is a one-coat type, achieving an advantage of simple configuration. The composite is prepared by mixing all the elements with a triple roll mill and forming into paste. Because the present embodiment provides good sensitivity and comparatively small temperature characteristics of sensitivity, it has a feature of ease in practical use.

Now referring to FIG. 1 to FIG. 32, there is shown a preferred embodiment of a gas sensor of the present invention.

(Embodiment 1)

FIG. 1 is a cross-sectional conceptual view of a gas sensor of one embodiment according to the present invention. In FIG. 1, numeral 1 is a gas detection element and numeral 2 is a gas selective permeation element. FIG. 1 shows a configuration in which the gas selective permeation element 2 covers at least part of the gas detection element. The gas detection element is are arranged with part in contact with the gas selective permeation element comprising part of a closed space and part separated. By the gas selective permeation element 2, of the components a, b, c, d in gas, part of components c, d are inhibited of entry because of diffusion and only a, b, detected gas components, are allowed to freely enter or go out. By detection of a, b, the gas detection element carries out gas detection operation. Because the gas components, which affect the characteristics and durability of the gas detection element are suppressed or inhibited of the contact with the gas detection element by the gas selective permeation element, the life of the gas detection element can be extended. For the gas detection element 1, various working principles such as contact combustion type, semiconductor type, solid electrolyte type can be applied.

The gas selective permeation element 2 is used by forming the pore-controlling membrane on the pore surface by a sol-gel process or CVD process using the ceramic porous body base material of pore sizes 0.1–1 $\mu$m prepared by sintering alumina, zirconia, etc. After forming ceramic porous base material and ceramic powders as they are or mixed with organic matter such as resin into a specified profile, it is fabricated by sintering at temperatures lower than that of perfect combustion. The mean pore size of the porous body fabricated by the sintering method is 0.1 $\mu$m at the limit. Consequently, in order to apply it to this invention, using the porous base material prepared by sintering, the pore must be treated with the coating membrane. Since the porous body fabricated by sintering is commercially available as the precision filtration membrane, in this invention, this commercially available product is used for the ceramic porous base material.

Now discussion will be made on the pore control method by the sol-gel process as follows. After hydrolyzing metal alkoxide such as zirconium isopropoxide, tetraethoxysilane, etc., it is polycondensed under catalyst conditions such as hydrochloric acid, etc. to prepare a desired sol solution. When this sol solution is brought in contact with porous ceramics with pores which can pass through this sol solution, for example, the porous ceramics are immersed in the sol, the sol solution is attracted by capillary force, and when this sol is dried, sol condensation and further gelation occur inside the pores of porous ceramics. As heating progresses further, sintering takes place from gelation and coating membrane is formed. As required, a method for filtering the sol solution using porous ceramics may be adopted. Using this method, the pore size control is enabled. By adjusting the wetting of pore surface of porous ceramics, sol solution, sol concentration, immersing time, and pull-out speed of ceramics, a gas selective permeation element with comparatively uniform pore sizes can be obtained.

In addition to the sol-gel process, using the CVD process, the pore control may be carried out by allowing the oxide membrane to form and grow inside pores of the porous body while pyrolyzing the compound in the flow system. This method is excellent for fabricating tubular porous bodies.

(Embodiment 2)

Figure 2:
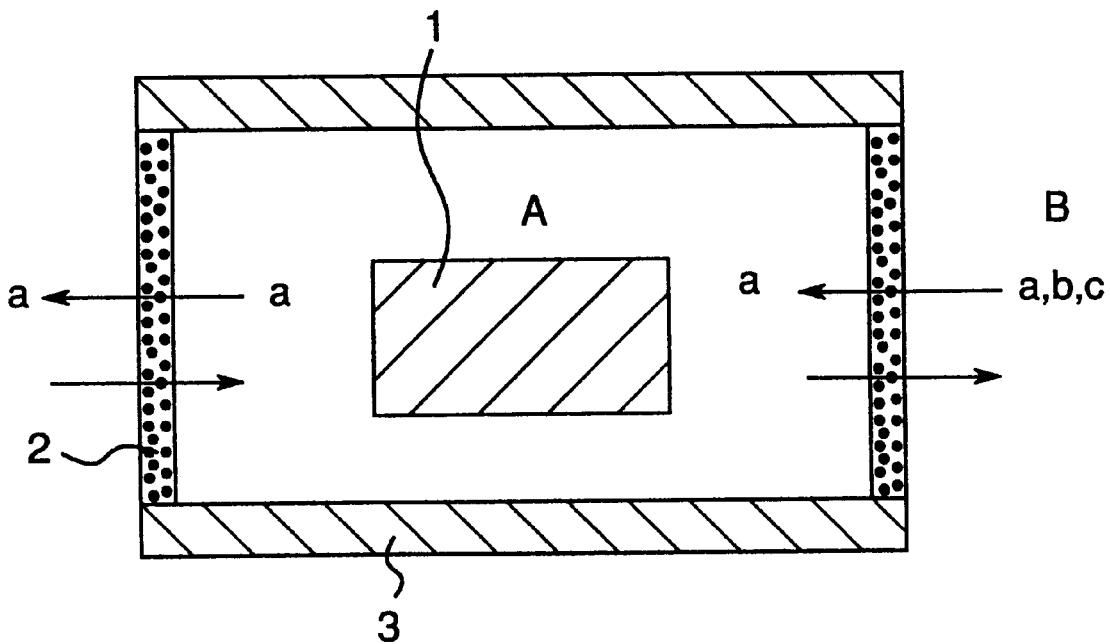
FIG. 2 is a cross-sectional view showing a gas sensor related to a second embodiment according to the present invention.

FIG. 2 is a cross-sectional conceptual view of a gas sensor of another embodiment according to this invention. In FIG. 2, the gas detection element 1 is housed inside the closed space comprising the base material 3 and gas selective permeation element 2 constituting at least part of the base material 3. The inside of closed space A and outside B pass the gas selective permeation element 2 only and allows the gas to go in and out. The gas selective permeation element 2 suppresses or blocks penetration of the gas components going in and out by the varying characteristics by the pore size and characteristics such as Knudsen diffusion, surface diffusion, and molecular sieves. Assuming that the gas components on the outside B of the closed space are a, b, c, only the gas component a of only the detected gas which the gas detection element is designed to detect is allowed to penetrate to the inside A of the closed space with this capability. By this effect, the operation of the gas detection element can be stabilized and the life of the gas detection element can be extended.

When the gas detection element is used by being housed in a closed space configured by arranging the gas selective permeation element as part of it, the requirements for the accuracy of the pore size of the gas selective permeation element becomes stringent. Because the gas selection effects of gas selective permeation element according to this invention are basically determined in accord with the pore diameter size, if the pore size has a wide distribution, gases other than the desired gas will flow in through pores of large pore size contained as defects. If the gas detection element works on a principle in which the ratio of some chemical characteristics is taken, for example, in the solid electrolyte system, since deterioration takes place in parallel on both sides of a pair of electrodes, apparent deterioration does not become conspicuous. Similarly, this system has less effects on the characteristics even if any changes due to clogging of the gas selective permeation element exists.

(Embodiment 3)

Figure 3:
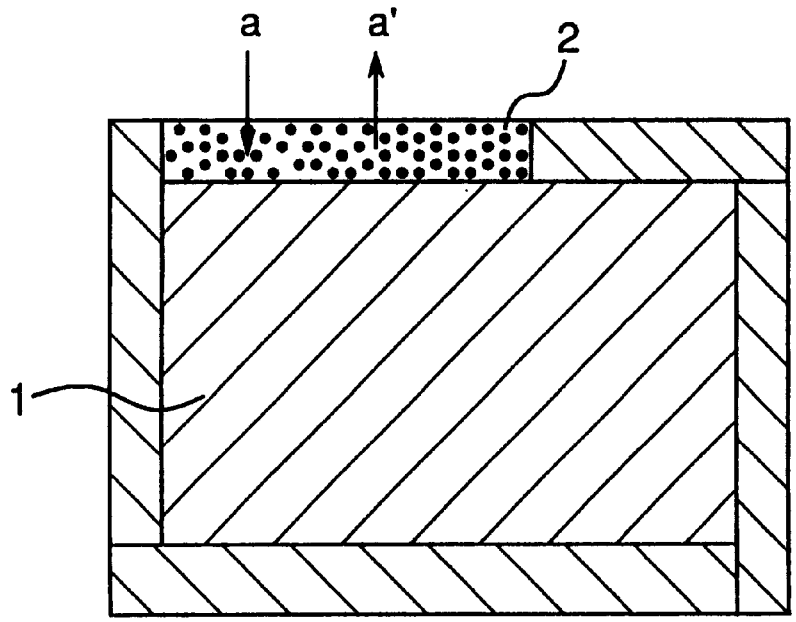
FIG. 3 is a cross-sectional view showing a gas sensor related to a third embodiment according to the present invention.

FIG. 3 shows a cross-sectional conceptual view of the gas sensor of another embodiment according to this invention. In FIG. 3, at least part of the gas detection element 1 is designed to be covered with the gas selective permeation element 2, and the gas detection element and the gas selective permeation element are brought into close contact and at the same time the detected gas component (a) comes into contact with the gas detection element 1 via the gas selective permeation element 2. In the case of the configuration in which elements 1 and 2 come in close contact in this way, as compared to Embodiment 2, the requirements for the accuracy on the pore size of the gas selective permeation element becomes slightly less stringent. Through large-size pores, a defect of the gas selective permeation element, other gases may enter, but even if this portion deteriorates, the functional portion of the gas detection element in contact with other normal pores is able to continue operation without any interference. However, if the gas selective permeation element is designed to come in close contact with the gas detection element, special consideration must be given, for example, to matching both thermal expansion coefficients. Effects on the durability are similar to those of the former embodiments.

(Embodiment 4)

Figure 4:
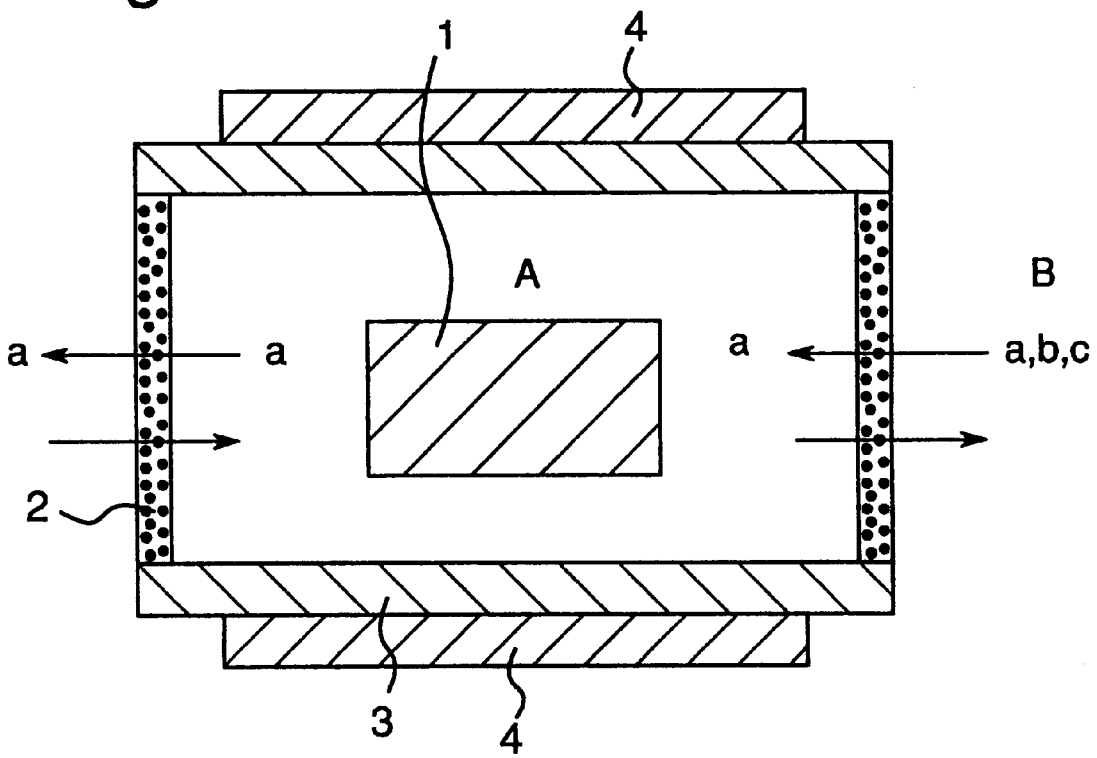
FIG. 4 is a cross-sectional view showing a gas sensor related to a fourth embodiment according to the present invention.

FIG. 4 shows a cross-sectional conceptual view of another embodiment according to this invention. In FIG. 4, a heating means 4 is newly added to the configuration of Embodiment 2. In FIG. 4, a closed space is formed by using in part the gas selective permeation element. Inside of the closed space the gas detection element 1 is housed, and the heating means 4 is arranged outside the gas selective permeation element 2, but the heating means may be arranged inside the closed space or in close contact with the gas detection element. Alternatively, the heating means may be arranged in the contact type gas sensor according to Embodiment 3. The heating means 4 may be contact-heated by forming iron-chrome or nichrome heating wire into a coil or forming a resistance membrane by thick film printing. With heating means 4, the gas sensor is heated to the temperature region required for the operation. Using a thermister, thermocouples, or other temperature detection means together with the heating means, temperature near the sensor may be detected and the sensor may be used with temperature controlled in combination with the heating means.

(Embodiment 5)

Figure 5A:
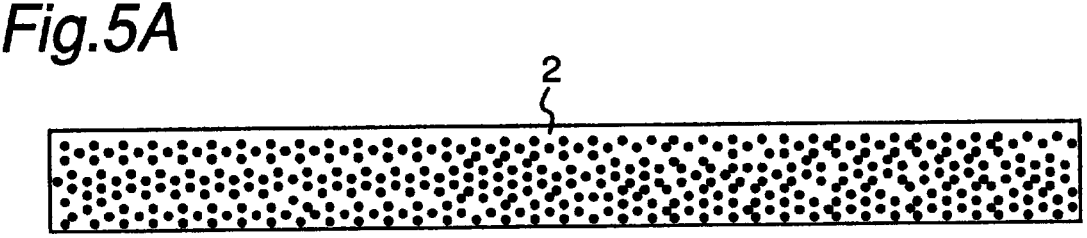
FIG. 5A is a cross-sectional view showing a gas selective permeation element related to a fifth embodiment according to the present invention.
Figure 5B:
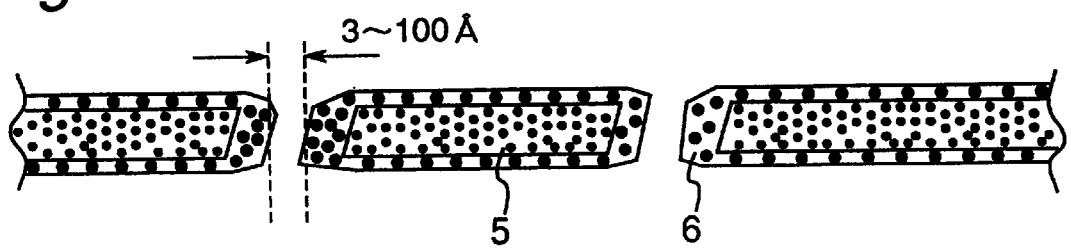
FIG. 5B is a cross-sectional view showing the gas selective permeation element related to the fifth embodiment according to the present invention.

FIG. 5A shows a cross-sectional conceptual view of gas selective permeation element of another embodiment according to this invention. In FIG. 5B, a pore-controlling membrane 6 is formed on the pore surface of the porous base material 5 and the mean pore diameter is controlled to 3–100 Å. Utilizing decomposition reaction of metal alkoxide (sol-gel process) or CVD reactions, the pore size can be controlled to the pore size in the molecular diffusion region. With these processes, the pore size can be controlled to uniform pores from 2 Å to several Å. This kind of pore size is the size of a gas molecule, and movement of gas in the pore has, in actuality, complicated diffusion characteristics in addition to the effects of interactions between the material on the pore surface and gases, but basically, the gas permeation rate is in the region from Knudsen diffusion to that of molecular sieves and is inversely proportional to the square root of the gas molecular weight or provides characteristics which markedly interfere with permeation of molecules with large molecular size. The molecule with large size is unable to pass the gas selective permeation element. By using the gas selective permeation element with the pores controlled to 3–100 Å, practically, to 5–100 Å, the selective permeability satisfactory for the use as a gas sensor is obtained.

Now description is made on the material of base material 5 of the gas selective permeation element. In particular, in the configuration in which the gas selective permeation element is used in close contact with the gas detection element, it is essential to match thermal expansion coefficients of the material of the base material of the gas selective permeation element and the material of the bulk main portion composing the gas detection element in order to constitute a gas sensor of high reliability. From this viewpoint, when a combination of solid electrolyte system with semiconductor type gas detection elements is considered for the gas detection element, alumina compounds or zirconia compounds should preferably be used for the base material of the gas selective permeation element.

For the material of pore-controlling membrane 6 used for pore control of the gas selective permeation element, zirconia, silica, or their mixture should preferably be used. It is in particularly effective when the gas selective permeation element is designed to have a mean pore diameter or 10 Å or less. Pores 10 Å or smaller indicate effective molecular sieve effects which do not pass high-molecular weight gases in a gas stream flowing from the outside to the inside of the gas selective permeation element. By the interaction with the gel membrane formed inside the pore, that is pore-control-treated membrane, selectivity is provided to gas permeability. That is, the intermolecular force between gas molecular and gel molecular has gas permeability selectivity, that is, surface diffusibility by the diffusing force based on the orientation force by interactions between permanent dipoles and electromotive force between permanent dipole and induced dipole, and van der Waals interaction, but hydrophobic pore-controlling membrane containing one or more types of silica or zirconia is free from any problem of pore blocking due to capillary condensation of water vapor, which constitutes a problem in applying a porous body with pore size in the region 10 Å or less, and is able to completely block the entry of the gas that deteriorates the gas detector 3 such as $SO_2$. In the gas detection element, even if $CO_2$ is formed as a result of catalyst reactions, it generally flows from the inside to the outside, and scarcely affects the operation of the gas detector. With the foregoing, a long-life operation of the gas detector can be guaranteed.

(Embodiment 6)

Figure 6:
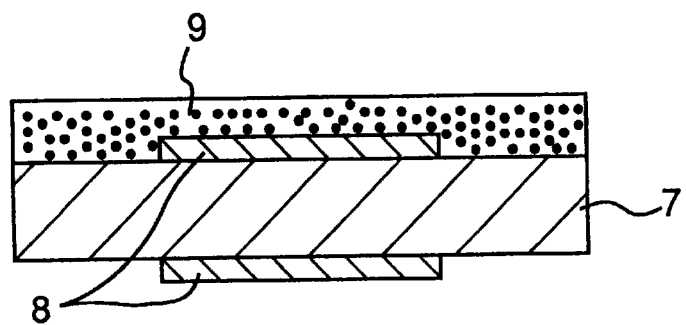
FIG. 6 is a cross-sectional view showing a gas detection element related to a sixth embodiment according to the present invention.

FIG. 6 shows a cross-sectional conceptual view of a gas detection element of another embodiment of this invention. In FIG. 6, the gas detection element is a solid electrolyte element equipped with an oxygen ion conductor 7, a pair of electrodes 8, and porous catalyst membrane 9. The solid electrolyte element of Embodiment 6 has a pair of electrodes 8 formed on both surfaces of the oxygen ion conductor 7 and porous catalyst membrane 9 is formed on one of the electrodes. For oxygen ion conductor 7, yttria stabilized zirconia or other oxygen ion conductor is used, and any shape such as flat plate, tubular, disc, column, etc. may be used. Electrode 8 may be formed by using any method of sputtering, electron beam evaporation, plating, or thick-film printing. However, the platinum electrode must be used for the electrode 8. Electrode 8 is formed on the front and rear surfaces, respectively, of the oxygen ion conductor 7 in FIG. 6, but it may be formed, for example, on any place, such as on the same surface or optional place on the surface of the oxygen ion conductor 7. However, the electrode profile and electrode forming conditions must be identical. For the porous catalyst membrane 9, the porous membrane formed by using glass or inorganic binder as a binding agent is used, in which oxidation catalyst such as transition metal oxide or noble metal is distributed or carried. The oxygen diffusibility and capability for oxidizing carbon monoxide are only required for the characteristics of porous catalyst membrane 9. Description is now made on the operation of this gas sensor. Depending on the temperature of the place equipped with a heating means or a sensor, the solid electrolyte element is heated to 400–500° C. required for operating the solid electrolyte element. In the case of air not containing carbon monoxide, oxygen diffuses into this element via the gas selective permeation element, but there is no difference in oxygen concentration between the catalyst side and naked electrode side, and no electromotive force based on the oxygen concentration difference is generated between both electrodes, and zero electromotive force is exhibited. Then, when air containing carbon monoxide is present, carbon monoxide and oxygen pass the gas selective permeation element and diffuse into the element. On the electrode on the catalyst side, carbon monoxide is oxidized in the catalyst layer and oxygen not containing carbon monoxide reaches the electrode and is adsorbed to the electrode surface, and is equilibrated with oxygen ion inside the solid electrolyte. On the other hand, on the naked electrode side, carbon monoxide and oxygen reach the electrode, and are both adsorbed on the electrode surface, but oxygen is oxidized by carbon monoxide and the adsorbed oxygen rate decreases and oxygen is equilibrated with oxygen ion inside the solid electrolyte under such condition. As a result, between both electrodes, an electromotive force based on the oxygen ion concentration difference is generated and carbon monoxide is detected. Arranging the gas detection element via the gas selective permeation element causes the electromotive force output to decrease, but causes no change in any responding speed, and the gases such as sulfur dioxide, etc. which have poisoning effects on the electrodes of the solid electrolyte and porous catalyst are blocked, and high durability is thereby achieved. Compared to the contact combustion system, it has advantages in that the zero point of the element is stabilized, the electromotive force output is great, and the element cost is low.

(Embodiment 7)

Figure 7:
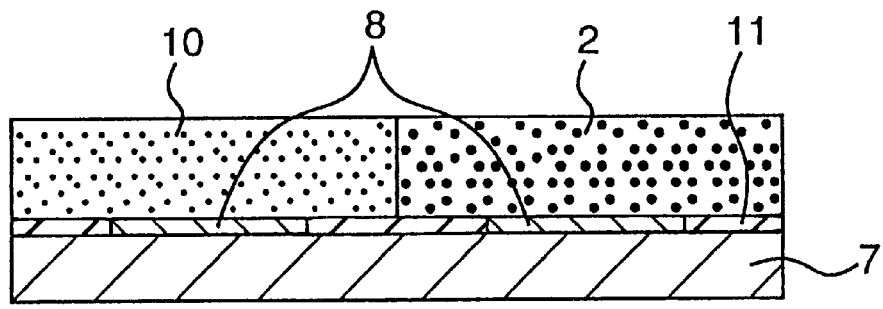
FIG. 7 is a cross-sectional view showing a gas detection element related to a seventh embodiment according to the present invention.

FIG. 7 shows a cross-sectional conceptual view of the gas detection element of another embodiment according to this invention. In FIG. 7, the gas detection element is a solid electrolyte element having an oxygen ion conductor 7 and a pair of electrodes 8, and a catalyst 10 is carried in pores in part of the region of the gas selective permeation element 2. The electrode 8 are insulated from each other by insulating material 11.

By carrying the oxidation catalyst in the pore of the gas selective permeation element, the same effects as those of porous catalyst membrane 9 according to Embodiment 6 can be obtained, and at the electrode on the region of the gas selective permeation element carrying the catalyst, carbon monoxide is oxidized with the catalyst and oxygen not containing carbon reaches the electrode and is adsorbed to the electrode surface, and is equilibrated with oxygen ion inside the solid electrolyte. On the other hand, on the naked electrode side, carbon monoxide and oxygen reach the electrode, and are both adsorbed on the electrode-surface, but oxygen is oxidized by carbon monoxide and the adsorbed oxygen rate decreases and oxygen is equilibrated with oxygen ion inside the solid electrolyte under such condition. As a result, between both electrodes, an electromotive force based on the oxygen ion concentration difference is generated and carbon monoxide is detected. The effects such as stability, durability, etc. are the same as those in the case of Embodiment 6.

(Embodiment 8)

Figure 8:
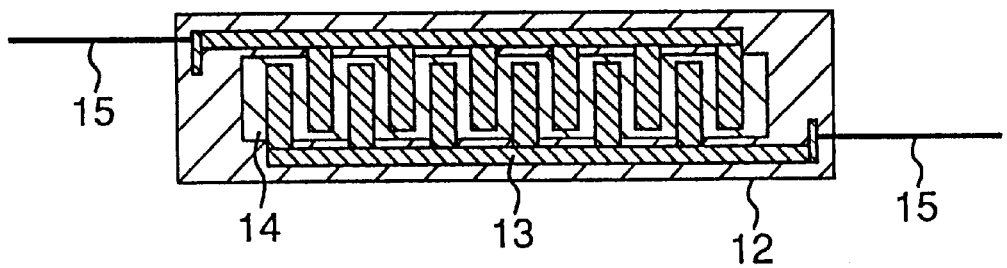
FIG. 8 is a cross-sectional view showing a gas detection element related to an eighth embodiment according to the present invention.

FIG. 8 shows a cross-sectional conceptual view of a gas detection element of another embodiment according to this invention. In FIG. 8, the gas detection element is a semiconductor element containing N type semiconductor composite 14. In FIG. 8, an interdigital electrode 13 is formed on the substrate 12, and on the surface of the interdigital electrode 13, an N type semiconductor compound 14 is formed. Numeral 15 is a lead wire for taking out the resistance change of this semiconductor element. For the base material 12, a heat-resistant insulating substrate such as alumina, etc. is used, and shapes including flat plate, tubular, columnar, and other various shapes are applicable. For the interdigital electrode 13, platinum, gold, and other electrodes formed by thick-film printing process, plating, or sputtering are used. When tubular or other base materials are used, electrodes are formed by a transferring process. The N type semiconductor membrane is obtained by mixing 0.1–10 $\mu$m N type semiconductor base oxide particles of stannic oxide, iron oxide, indium oxide, zinc oxide, etc. with palladium, platinum, or other noble metal sensitizer, a porous agent represented by cellulose derivatives such as carobxymethyl cellulose, and glass used for binding agent together with organic solvents to make a paste, then, drying and sintering after applying the paste to the base material.

With the membrane heated to a specified temperature by a heating means, etc., the N type semiconductor membrane 14 has the inside electrons trapped by oxygen entering from the gas selective permeation element and is held in the high resistance state. When air containing carbon monoxide comes in contact with the gas sensor, the trap is released by carbon monoxide entering from the gas selective permeation element 2 and the N type semiconductor membrane changes to the low resistance state, and carbon monoxide is thereby detected. The N type semiconductor oxides such as stannic oxide, iron oxide, indium oxide, zinc oxide, etc. adsorb oxidizing gas such as sulfur dioxide, etc. and deteriorate, but the entry of oxidizing gas to the semiconductor detection element is completely blocked by the gas selective permeation element, and therefore, the semiconductor element will not deteriorate and long-life operation can be expected. The semiconductor element provides large temperature characteristics and poses a problem of unstable operation with respect to temperature change, but in this embodiment, setting the operation to high-temperature operation exceeding 200° C. causes the temperature dependency of the gas sensor to change the rate-control process from activation control of the semiconductor element to diffusion control of the porous body, and the temperature dependency can be extremely reduced, and stable operation with respect to temperature can be expected. This is because in the case of activation control, the reaction speed changes exponentially with respect to temperature but in the case of diffusion control, it changes by about three-seconds power to temperature.

However, in this case, for the N type semiconductor membrane, it is necessary to adopt highly sensitive material even for the high-temperature side. In the conventional technique, in order to secure the stability of semiconductor element, low-temperature operation at 100–150° C. and high-temperature operation at 300–350° C. were repeated and during the low-temperature operation, the operation was set to the gas detection operation mode, and during the high-temperature operation, it is set to the regeneration mode. Therefore, for the information on gas concentration, only intermittent data was able to be collected, for example, once per 1 minute, but with this configuration, stable continuous operation on the high-temperature side is enabled.

(Embodiment 9)

Figure 9:
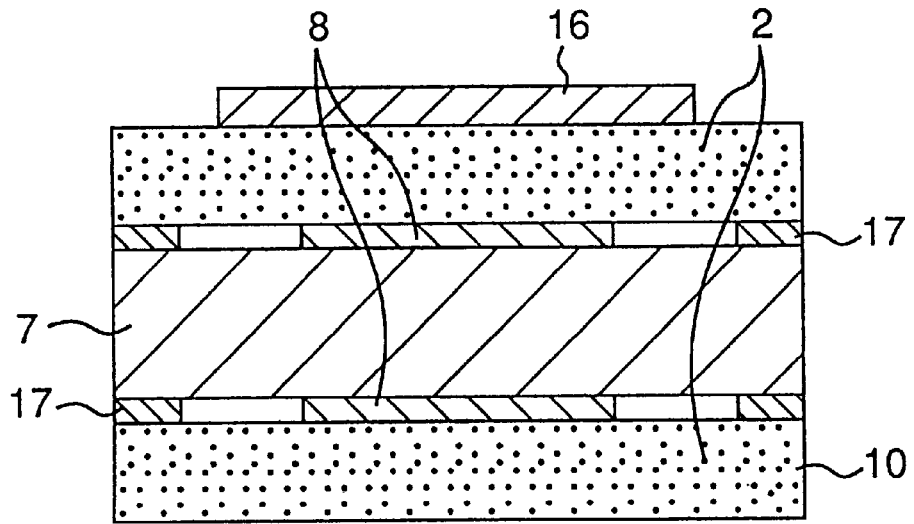
FIG. 9 is a cross-sectional view showing a gas sensor related to a ninth embodiment according to the present invention.

FIG. 9 shows a cross-sectional conceptual view of the solid electrolyte type gas sensor of another embodiment according to this invention. In FIG. 9, the gas sensor comprises a pair of gas selective permeation element 2, oxidation catalyst carried on one of the gas selective permeation elements, a heating membrane 16 laminated on one surface of the other gas selective permeation element, an electrode membrane 8 on the opposite side surface, oxygen ion conductor membrane 7, and then another electrode membrane 8 is in turn laminated, wherein these are oppositely arranged and sealed with sealing material 17. For sealing material, glass and inorganic adhesives are used with the thermal expansion coefficients matched between the oxygen ion conductor and gas selective permeation element. Temperature required for operating the solid electrolyte element is achieved by a heating means 16. When gas containing carbon monoxide is fed to the gas sensor according to this embodiment, a concentration cell type electromotive force is generated between electrodes in contact with the gas selective permeation element carrying the catalyst and the gas selective permeation element not carrying the catalyst, and carbon monoxide is detected. The effects, etc. related to durability of the sensor according to this embodiment are same as those described above.

(Embodiment 10)

Figure 10:
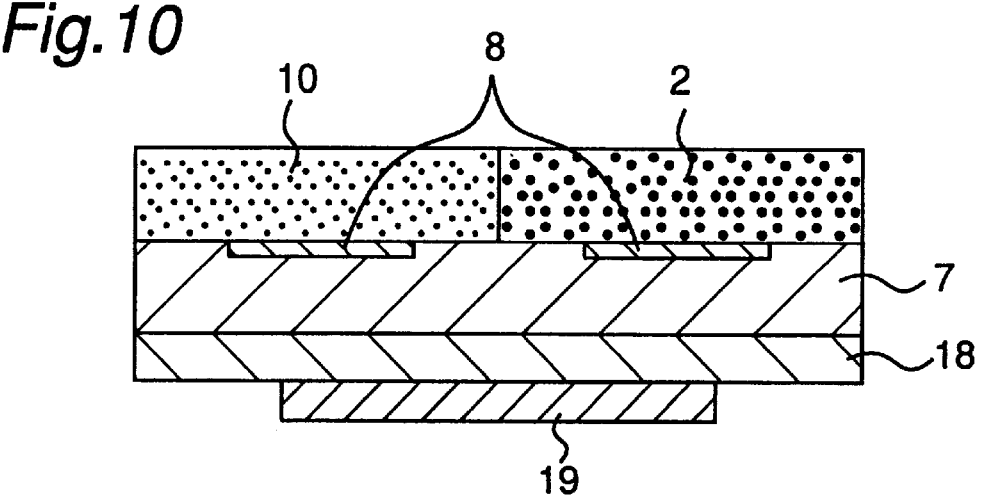
FIG. 10 is a cross-sectional view showing a gas sensor related to a tenth embodiment according to the present invention.

FIG. 10 is a cross-sectional conceptual view of the solid electrolyte type gas sensor of another embodiment according to this invention. In FIG. 10, the oxidation catalyst 10 is carried in the pores of part of the region of the gas selective permeation element 2, and in the region of this gas selective permeation element carrying the oxidation catalyst and in the region not carrying the catalyst, electrodes 8 are formed, respectively, and to this pair of electrodes 8, an oxygen ion conductor layer 7, ceramic insulator layer 18, and heating coated layer 19 are laminated in turn. The temperature from 300 to 500° C. required for operation of this sensor is achieved by the heating membrane 19. When the sensor comes in contact with air containing carbon monoxide, gas molecules enter the element inside through the gas selective permeation element 2 only. With respect to the pair of electrodes 8, on the left side layer, air entering the electrode enters while passing the gas permselective membrane portion carrying the oxide catalyst 10 in the pores, where carbon monoxide is oxidized, and carbon monoxide is not able to reach the electrode. As against this, on the right side electrode, carbon monoxide enters as it is and reaches the electrode. With this configuration, the electromotive force is obtained and carbon monoxide is detected. The effects, etc. related to durability of the sensor according to this embodiment are same as those described above.

(Embodiment 11)

Figure 11:
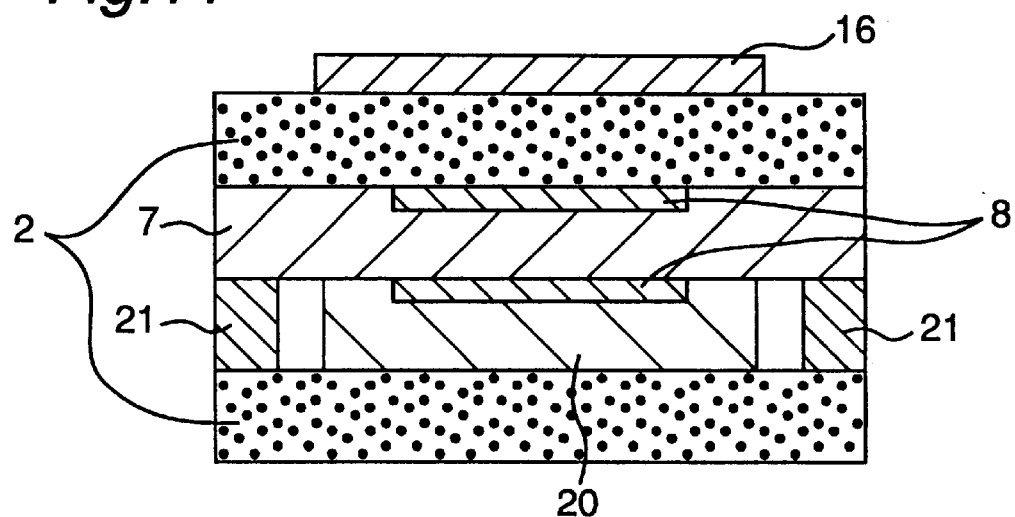
FIG. 11 is a cross-sectional view showing a gas sensor related to an eleventh embodiment according to the present invention.

FIG. 11 is a cross-sectional conceptual view of a solid electrolyte type gas sensor of another embodiment according to this invention. In FIG. 11, this gas sensor comprises a pair of flat plate type gas selective permeation elements 2, a heating membrane 16 provided on one side of one of the gas selective permeation elements, electrode membrane 8, oxygen ion conductive solid electrolyte membrane 7, and another electrode membrane 8, and porous catalyst membrane 20 in turn laminated on the rear side, the other selective permeation element is oppositely arranged on the porous catalyst membrane 20, and sealing material 21 for sealing the permeators. The sealing material 21 is the same as that used in Embodiment 9. Temperature from 300 to 500° C. required for operation of this sensor is realized by the heating membrane 16. The operation of the gas sensor is basically the same as that described in Embodiment 6. The effects, etc. related to durability of the sensor according to this embodiment are once the same as those described above.

(Embodiment 12)

Figure 12:
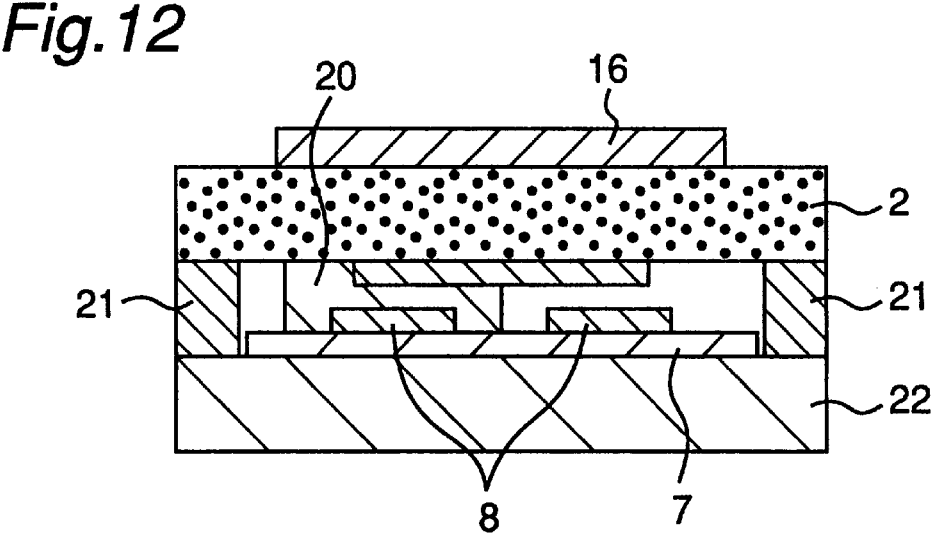
FIG. 12 is cross-sectional view showing a gas sensor related to the twelfth embodiment according to the present invention.

FIG. 12 is a cross-sectional conceptual view of a solid electrolyte system gas sensor of another embodiment according to this invention. In FIG. 12, the gas sensor comprises oppositely arranging a plate type gas selective permeation element 2 with a heating membrane 16 formed on one side, and a pair of electrodes 8 arranged on the same surface of an oxygen ion conductive solid electrolyte membrane 7 and a ceramic insulation plate 22 equipped with a porous catalyst coated layer 20 mounted above one of the electrodes and sealing them with the sealing material 21. Though the basic arrangement differs, operation, etc. are the same as those of Embodiment 11. The effects, etc. related to durability of the sensor according to this embodiment are the same as those described above.

(Embodiment 13)

Figure 13:
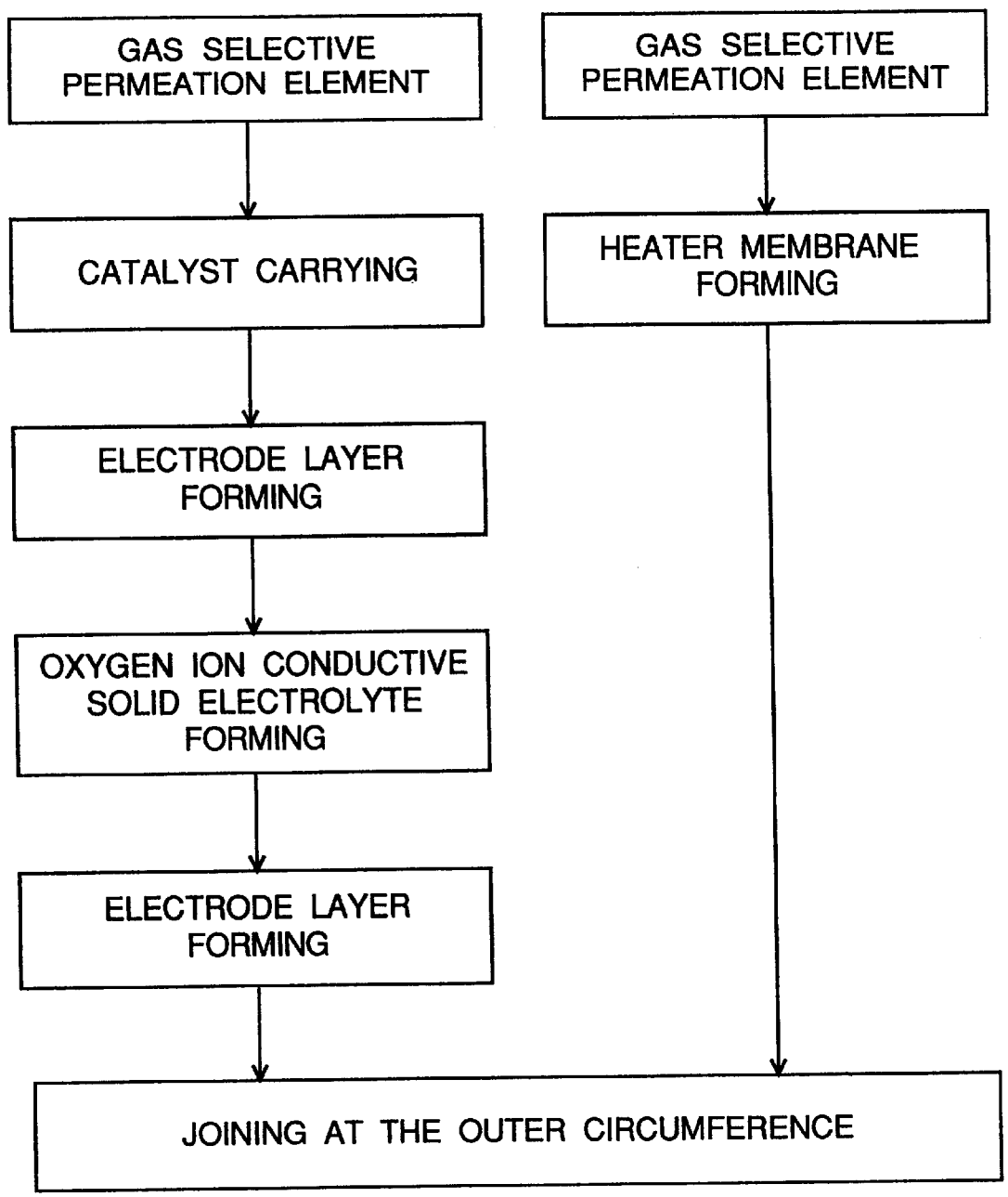
FIG. 13 is an explanatory diagram showing the manufacturing process the gas sensor related to a thirteenth embodiment according to the present invention.

FIG. 13 shows a manufacturing method of a solid electrolyte system gas sensor of other embodiment according to this invention. The gas selective permeation element is fabricated by filling pores with ceramic thin film using commercially available ceramic porous membrane by the use of the sol-gel process or CVD process. Then, for a method for carrying oxidation catalyst to pores in part of the region of pores, examples include a method for carrying noble metal by CVD and other method and a method for dipping part of the gas selective permeation element in the noble metal aqueous solution, drying, sintering, and reducing with a reducing agent as required. For the type of catalyst carried in the pore, from the viewpoint of sizes of dispersibility of catalyst particles, noble metal is preferable and in particular, palladium and rhodium are best. When it is operating as a gas sensor, 300–500° C. temperature exists, and the catalyst is able to exhibit its capabilities sufficiently at the level of reaction time during gas diffusion in the pore.

A pair of platinum electrode membranes are fabricated by a membrane forming means such as electron beam deposition process, ion plating process, or sputtering with the non-electrode forming portion covered with a masking jig. In this event, the gas selective permeation element should be preferably heated. This is to obtain satisfactory interlayer adhesion. The membrane may be formed by paste printing using a screen printing process. In this event, characteristics of the electrode degrade. This is attributed to high temperature exceeding 900° C. required for sintering, which degrades the porosity of the electrode. Under this condition, lead wires such as platinum wires are joined to the electrodes, and over this, oxygen ion conductive solid electrolyte membrane is formed by a membrane forming method such as sputtering or laser ablation. The membrane thickness of 1 $\mu$m to 10 $\mu$m is enough. Excessively thin membrane degrades the quality of membrane, causing a fear of generating oxygen permeability, and conversely if the thickness exceeds 10 $\mu$m, it takes time for forming membrane and costs high, and a problem of cracking occurs in the element due to thermal stress among laminated materials with different thermal expansion coefficients. When the method of fabricating electrode membrane differs from that of oxygen ion conductive solid electrode membrane, vacuum must be released every time, and operating conditions such as vacuum must be changed every time, which is quite troublesome. In the case of sputtering, vacuum must be released for replacing masking jigs, which is also troublesome, but this is advantageous because the gas sensor can be fabricated in a consistent procedure. The gas selective permeation element fabricated in this way and a gas selective permeation element with the heating membrane formed by thick film printing, etc. are joined at their circumference with inorganic adhesives or glass, etc. to make a gas sensor. The gas sensor fabricated by the above process can be made generally small-size and thin. Consequently, low power consumption is achieved. Since the gas diffusion space reaching above the electrode is small, high-speed responsibility can be achieved. In addition to the foregoing, with respect to electrode deterioration, since the electrode is partitioned with ceramic gas permselective membrane, even if there is a structural defect in the permselective membrane and a large hole is open, the other pore portion free of trouble prevents the interfering gas or gas deteriorating the electrode from reaching the electrode, overall deterioration on the electrode surface can be prevented. Since the catalyst is formed within pores, it is not subjected to the influence of interference gas with large molecular size and longer life is secured.

(Embodiment 14)

Figure 14:
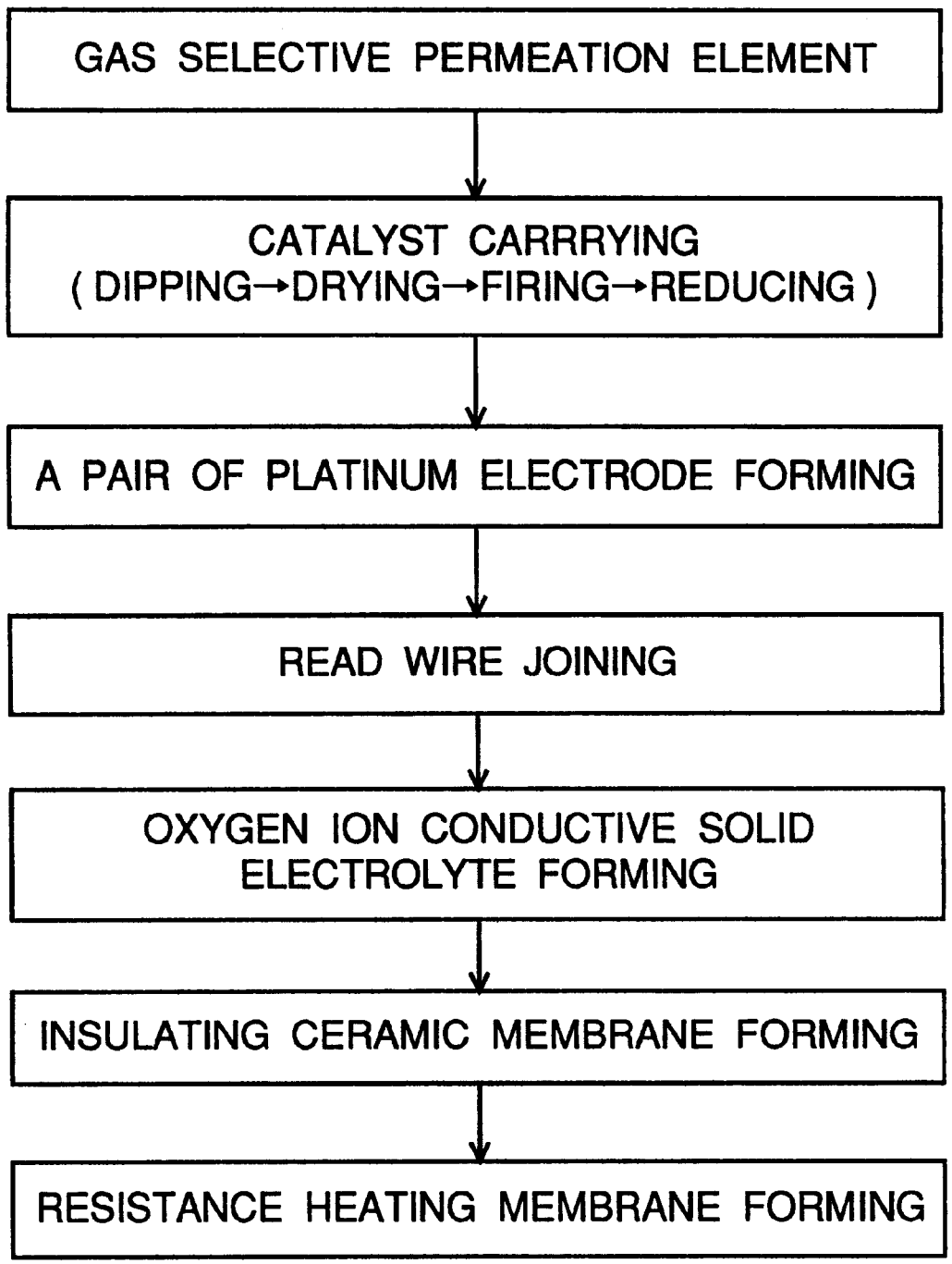
FIG. 14 is an explanatory diagram showing a manufacturing process the gas sensor related to a fourteenth embodiment according to the present invention.

FIG. 14 shows a manufacturing method of solid electrolyte system gas sensor of another embodiment according to this invention. It is nearly similar to the preceding process, but the method for carrying platinum group elements in pores of part of the region of the gas selective permeation element is the same as that described before, and the gas sensor is fabricated by a method for carrying noble metal by a method such as CVD after masking the untreated region in advance, or a method for drying, sintering, and reducing as required using a reducing agent after part of the gas selective permeation element is dipped in the noble metal aqueous solution. Others are same as that in the case of Embodiment 13.

(Embodiment 15)

Figure 15:
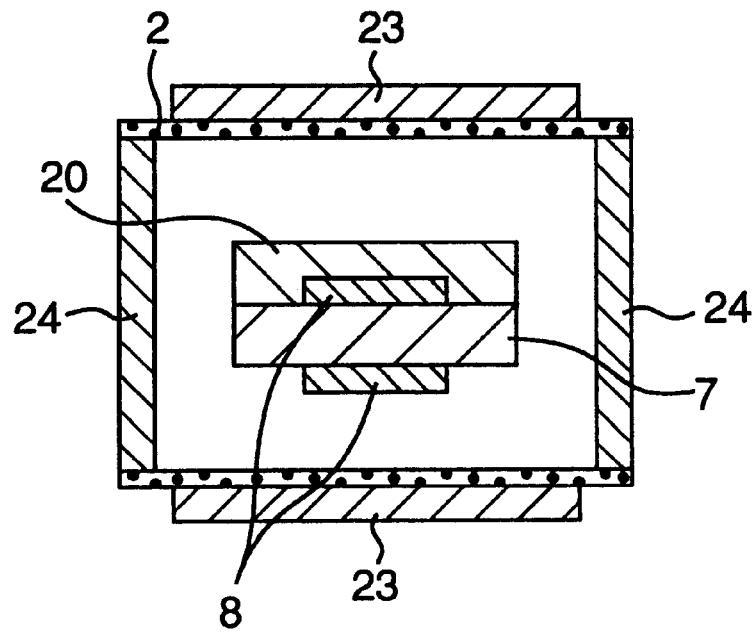
FIG. 15 is a cross-sectional view showing a gas sensor related to a fifteenth embodiment according to the present invention.

FIG. 15 shows a cross-sectional conceptual view of the solid electrolyte system gas sensor of another embodiment according to this invention. In FIG. 15, this gas sensor comprises a pair of electrode membranes 8 provided on both surfaces, an oxygen ion conductor 7 with a porous oxidation catalyst layer 20 provided on one of the electrodes housed in a tubular gas selective permeation element 2, and a heating means 23 provided around the circumferential portion.

Description is made on the fabricating method of the tubular type gas selective permeation element. Description is also made on the control method of pore size of porous membrane by the sol-gel process. Basically, a ceramic porous body with 1-micron level pores which is in general commercially available as precision filtering membrane is used as a base material and by closing the pores, the tubular gas selective permeation element is fabricated. After pyrolyzing metal alkoxide such as aluminum isopropoxide and tetraethoxysilane, it is polycondensed under the catalyst condition such as hydrochloric acid, etc. to make a sol solution. When this sol solution is brought in contact with the hydrophilic porous ceramic with pores through which this sol solution can permeate, water is adsorbed by capillary force, and in the porous ceramic or glass pores, sol condensation, and further gelation occur. As required, a method for filtering the sol solution using a porous ceramics can be adopted. Using this phenomenon, the pore size can be controlled. When the porous ceramic pores are brought into contact with the sol aqueous solution obtained from metal alkoxide, specifically, when porous ceramics are dried after immersed in the sol solution for a short time, gelation occurs in pores and the pores close. Adjusting the wettability of pore surface of base material, sol concentration, and immersing time, it is possible to carry out uniform pore diameter control at 2 to several Å level. Pore control may be carried out by allowing oxides to form and flow in the porous pores while thermal decomposing compounds such as alkoxide in the flow system by the CVD process in addition to the sol-gel process. This process is more excellent for a process to fabricate a tubular uniform gas selective permeation element.

The operation of the solid electrolyte system gas detection element housed in the tubular gas selective permeation element is same as in the case of preceding Embodiments. Tubular gas sensors provide strong thermal impact, etc. and excellent applicability under severe environment such as combustion exhaust gas flow, etc. The effects, etc. related to durability of the sensor according to this embodiment are same as those described above.

(Embodiment 16)

Figure 16:
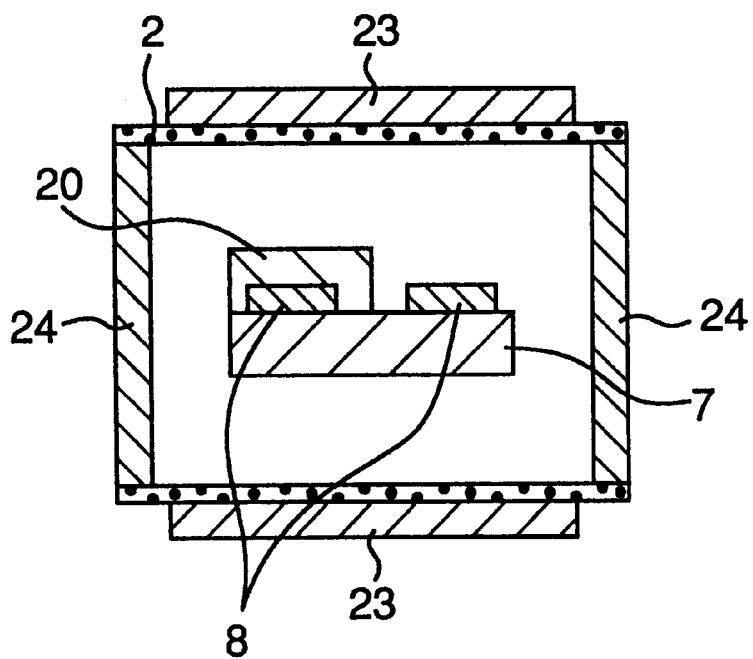
FIG. 16 is a cross-sectional view showing a gas sensor related to a sixteenth embodiment according to the present invention.

FIG. 16 is a cross-sectional conceptual view of a solid electrolyte system gas sensor of another embodiment according to this invention. In FIG. 16, this gas sensor comprises a pair of electrode membranes 8 on one side, a plate form oxygen ion conductor 7 with a porous oxidation catalyst layer 20 mounted on one electrode housed in the tubular gas selective permeation element, and a heating means 23 provided on its circumferential portion. In this embodiment, electrodes are arranged on the same surface as that of plate-form oxygen ion conductor. Because the electrode is located on the same plane, the electrode forming process is simplified and is advantageous in terms of cost. The effects, etc. related to durability of the sensor according to this embodiment are same as Embodiment 15.

(Embodiment 17)

Figure 17:
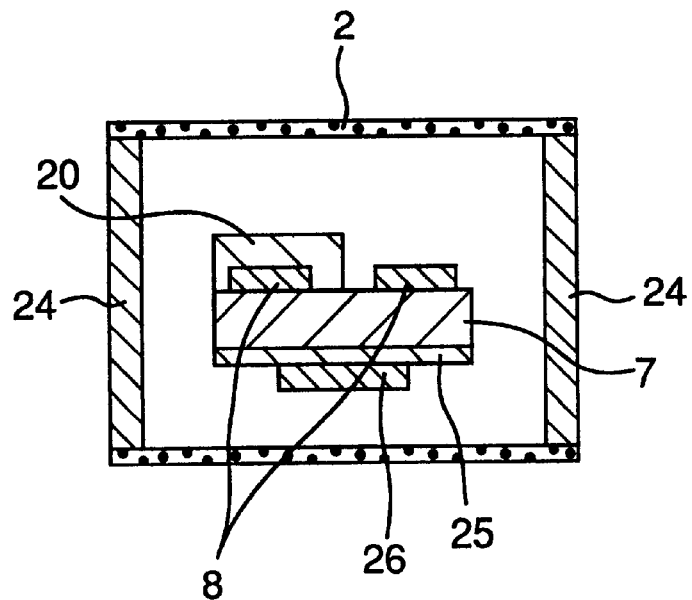
FIG. 17 is a cross-sectional view showing a gas sensor related to a seventeenth embodiment according to the present invention.

FIG. 17 is a cross-sectional conceptual view of the solid electrolyte system gas sensor of other embodiment according to the present invention. In FIG. 17, this gas sensor comprises a pair of electrode membranes 8 on one side, non-electrode forming surface of the plate-form oxygen ion conductor 7 equipped with porous oxidation catalyst layer 20 on one of the electrodes is joined with non-heating membrane surface of the insulation plate 25 equipped with a heating membrane 26, and this joined plate form oxygen ion conductor and the insulation plate are housed in the tubular gas selective permeation element 2. In FIG. 17, temperature required for operation of the gas sensor is obtained from the heating membrane 26. The gas sensor of this embodiment is fabricated in the following procedure.

On the insulation plate 25 with the heating membrane 26 fabricated on the rear side, an oxygen ion conductive solid electrolyte layer 7 is fabricated. To this, any of the wet process such as the sol-gel process, or the dry process such as sputtering process or laser ablation process can be applied. On this solid electrolyte layer 7, a pair of platinum electrodes 8 are fabricated. For the electrode forming process, those described as above are applicable. On one of this pair of electrodes 8, a porous oxidation catalyst membrane 20 is formed. For this, application of the wet process is more preferable than the dry process. This is because the wet process is advantageous in forming composite membrane containing a porous main catalyst and its promoter. On the electrode side of the element formed in this way, gas selective permeation element is sealed using a sealing material such as glass to fabricate a gas sensor. In the case of FIG. 17, gases to be detected all pass the tubular gas selective permeation element 2 with controlled pores and reach the catalyst 20 and the electrode 8, and the similar effects are expected. The manufacturing method of sensors is quite productive.

(Embodiment 18)

Figure 18:
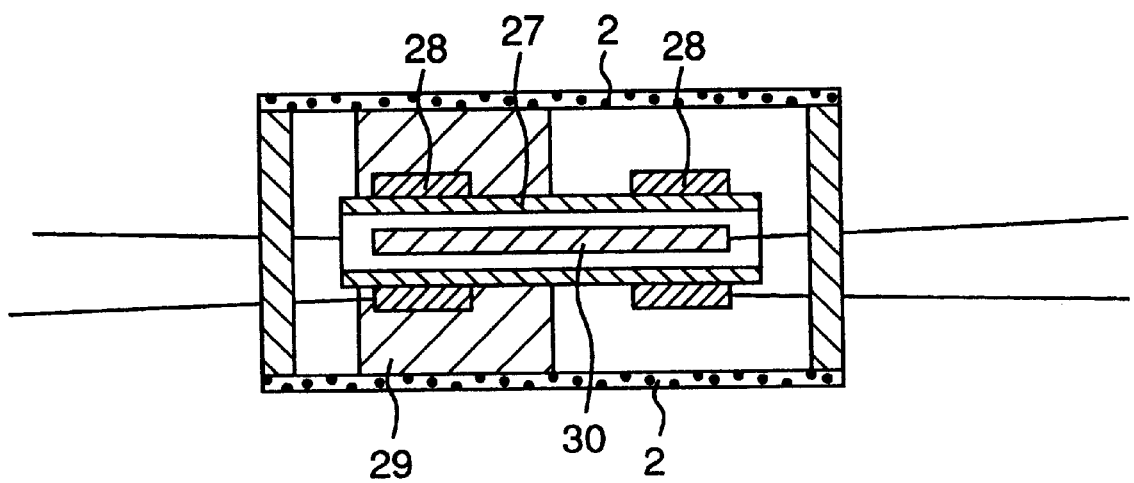
FIG. 18 is a cross-sectional view showing a gas sensor related to an eighteenth embodiment according to the present invention.

FIG. 18 is a cross-sectional conceptual view of a solid electrolyte system gas sensor of another embodiment according to this invention. In FIG. 18, this gas sensor houses in the tubular gas selective permeation element 2 a tubular oxygen ion conductor 27 with a pair of electrode membranes 28 on the outer surface, a porous oxidation catalyst layer 29 on one of the electrodes, and the heating wire 30 contained inside.

The tubular oxygen ion conductor 27 is fabricated by sintering after forming by extrusion or pressing. The electrode can be formed on this surface by various known conventional membrane forming processes but from the viewpoint of achieving good adhesion with the oxygen ion conductor and sufficient porosity simultaneously, a dry process such as electron beam deposition process, ion plating process, or sputtering process is desirable. Patterning of the electrode is carried out by masking using jigs. The porous oxidation catalyst layer 29 is formed on the electrode by the process using paste similar to that in the case of the preceding flat plate type. For the heating wire 30, general electric heating wire such as iron chrome or nichrome. The operation and characteristics of the gas sensor of this embodiment are same as those of the preceding embodiment.

(Embodiment 19)

Figure 19:
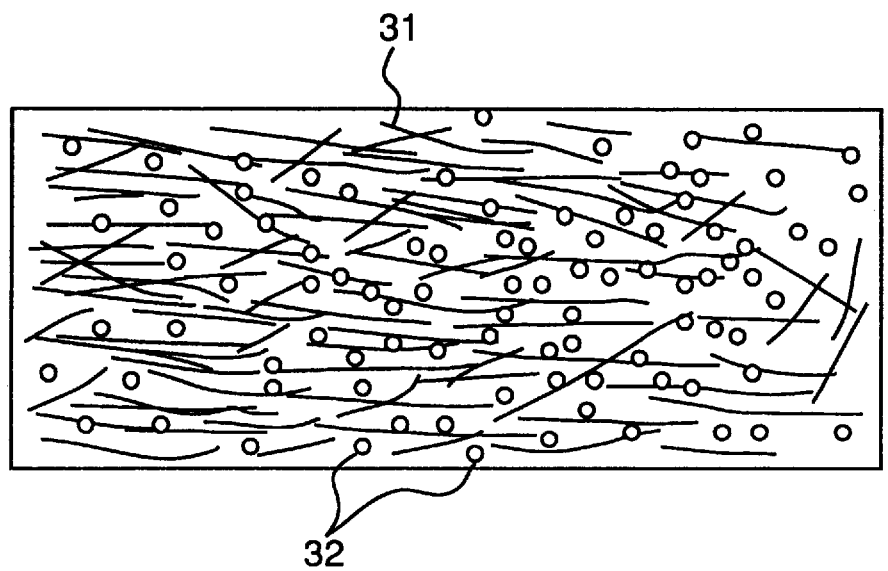
FIG. 19 is a cross-sectional view showing a gas catalyst membrane related to a nineteenth embodiment according to the present invention.

FIG. 19 shows a cross-sectional conceptual view of porous catalyst membrane 20 of another embodiment according to this invention. In FIG. 19, the porous catalyst membrane comprises ceramic paper formed by mixing and papermaking oxidation catalyst particles 32 with ceramic fiber 31. This ceramic paper is fabricated by dispersing oxidation catalyst powder carried together with noble metal element on transition metal oxidation catalyst powder such as iron, manganese, copper, nickel, cobalt, chromium, etc. or porous carrier such as alumina, etc. in water together with ceramic fibers such as silica.alumina fibers, and inorganic binding agent such as alumina sol or colloidal silica, and then filtering, compressing, and drying. Because the porous catalyst membrane of this embodiment holds the condition in which the oxidation catalyst fulfilling its capabilities is uniformly dispersed in the matrix and at the same time provides excellent diffusibility of oxygen, porous catalyst membrane with extremely excellent features can be formed.

(Embodiment 20)

Figure 20:
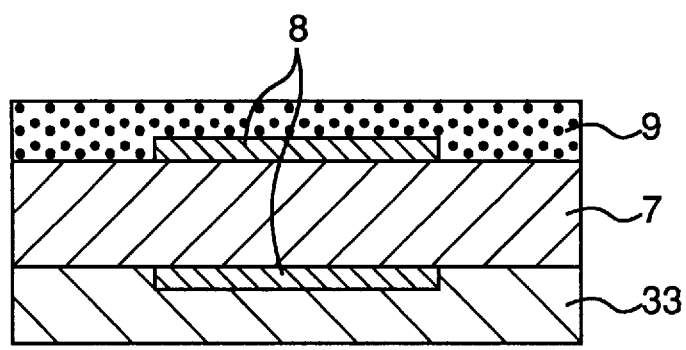
FIG. 20 is a cross-sectional view showing a solid electrolyte element related to a twentieth embodiment according to the present invention.

FIG. 20 is a cross-sectional conceptual view of solid electrolyte element of another embodiment according to this invention. In FIG. 20, a non-oxidizing porous layer 33 is formed on one electrode on the side without porous catalyst membrane 9 of a pair of electrodes 8 on the oxygen ion conductor 7. With respect to the solid electrolyte element which does not form non-oxidizing porous layer, strictly speaking, there is a subtle difference in oxygen diffusibility between the electrode with the porous catalyst membrane formed and the naked electrode, and with this, it has a problem in that under the condition free of carbon monoxide, the zero point slightly shifts. By providing a non-oxidizing porous layer, this balance can be adjusted. Depending on the conditions of gas selective permeation element, there is a case in which the inflow of poisoning gas is unable to be completely blocked, and it bears a function for protecting the electrode from being poisoned. The operation as a gas sensor is same as that described above. The characteristics are also same as those described above. Since the non-oxidizing porous layer has a fear of deformation or changing gas diffusibility and impairing the stability when moisture is adsorbed, it is preferable to use materials with silica or zirconia with excellent moisture resistance used as main components.

(Embodiment 21)

Figure 21:
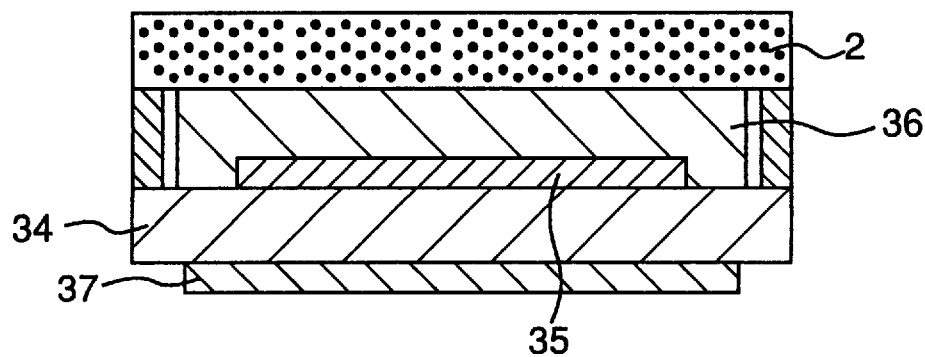
FIG. 21 is a cross-sectional view showing a gas sensor related to a 21st embodiment according to the present invention.

FIG. 21 is a cross-sectional conceptual view of a semiconductor type gas sensor of another embodiment according to this invention. In FIG. 21, the gas sensor of this embodiment comprises a pair of interdigital electrode 35 on one surface of the insulation substrate 34 and N type semiconductor oxide system sinter membrane 36 on the electrode, wherein the electrode surface side of the substrate 34 with the heating membrane 37 equipped on the other surface is joined to seal with the plate form gas selective permeation element 2. Via the gas selective permeation element 2, restricted gas goes in and out to and from the semiconductor element. The operation and characteristics of the gas sensor of this embodiment are same as those described above.

(Embodiment 22)

Figure 22:
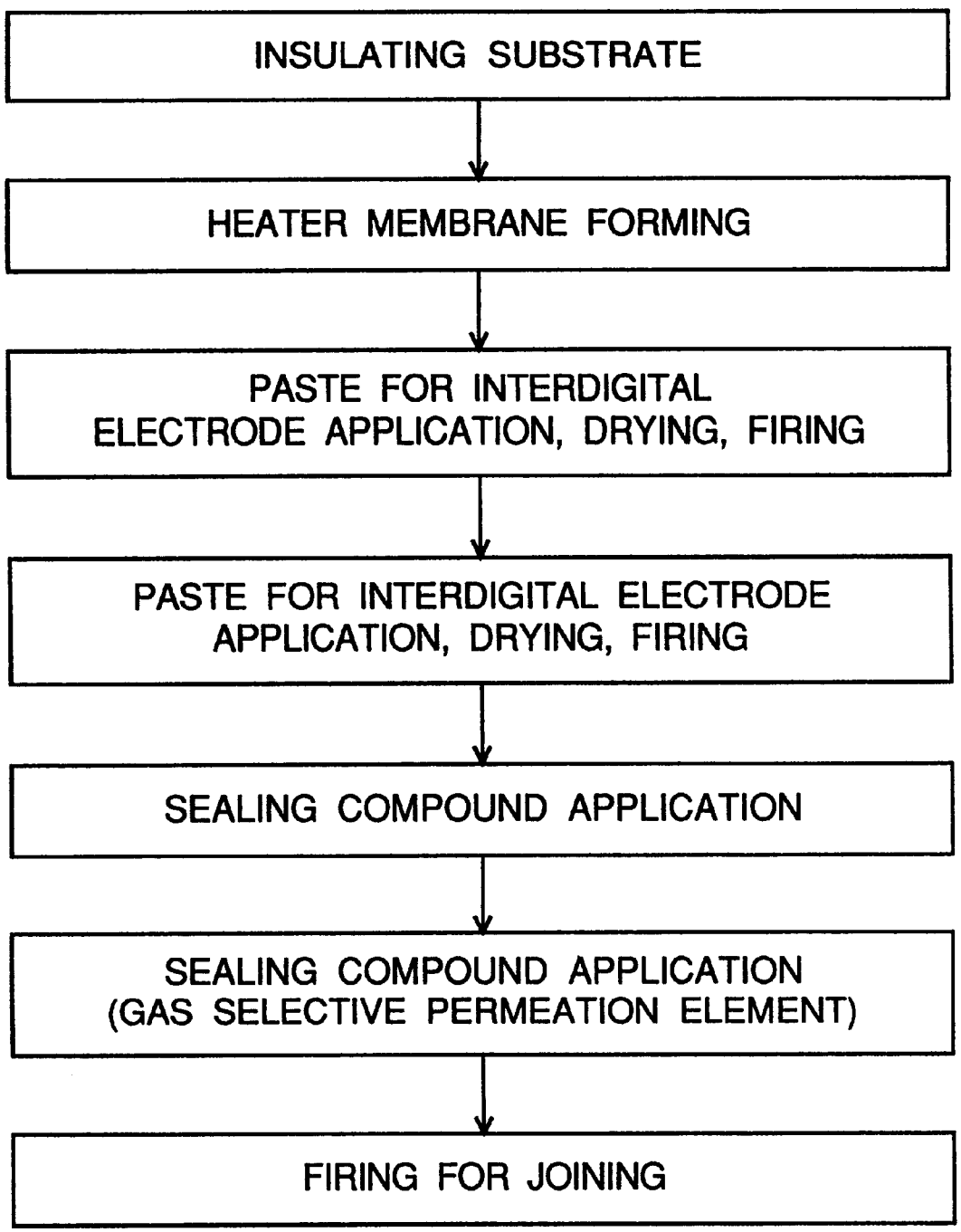
FIG. 22 is an explanatory diagram showing a manufacturing process a gas sensor related to a 22nd embodiment according to the present invention.

FIG. 22 is a flow chart showing a manufacturing process of a semiconductor system gas sensor of the embodiment 21 according to this invention. On one side of the insulation substrate, a heater membrane is formed by either plating or thick-film printing process, and on the other surface, a pair of interdigital electrode and N type semiconductor oxide system sinter membrane are formed, respectively, by the thick-film printing process; then, they are sealed by joining with the plate form gas selective permeation element to manufacture a gas sensor. In either case, a thick-film printing process with excellent productivity is used, and there is an advantage of manufacturing the gas sensor at low cost.

(Embodiment 23)

Figure 23:
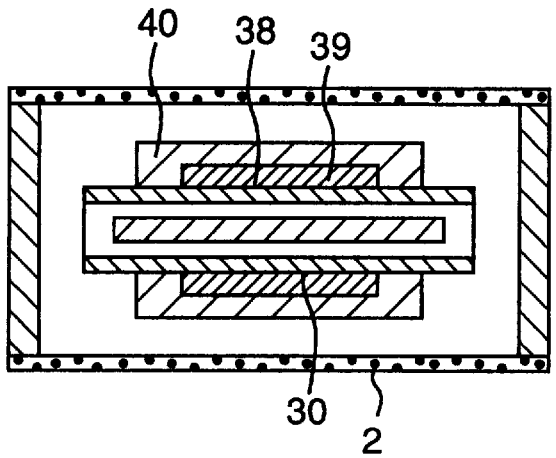
FIG. 23 is a cross-sectional view showing a gas sensor related to a 23rd embodiment according to the present invention.

FIG. 23 is a cross-sectional conceptual view of the semiconductor type gas sensor of another embodiment according to this invention. In FIG. 23, the gas sensor of this embodiment is formed by forming a pair of interdigital electrode membrane 39 on the outer surface of the tubular insulation substrate 38, laminating N type semiconductor oxide system coated layer 40 on this electrode membrane 39, and housing, in the tubular gas selective permeation element 2, a gas detection element with a heating wire 30 arranged in the tube inside. For the tubular insulation substrate, commercially available hollow tubes such as alumina, cordierite, etc. is used. The interdigital electrode membrane to the tubular insulation substrate is formed preferably by the stage printing process or transferring process. For a semiconductor system, a highly reliable and high productivity gas sensor is obtained. The operation and characteristics of the gas sensor of this embodiment are same as those described above.

(Embodiment 24)

Figure 24:
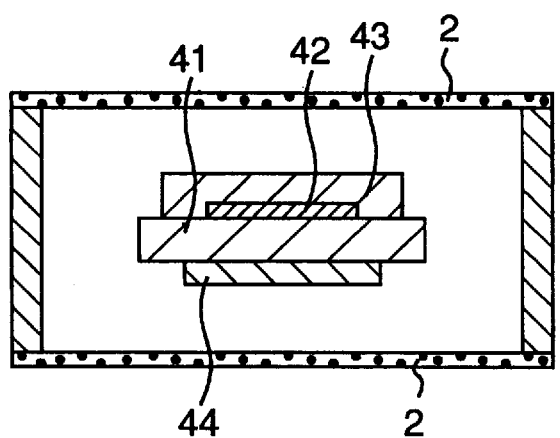
FIG. 24 is a cross-sectional view showing a gas sensor related to a 24th embodiment according to the present invention.

FIG. 24 is a cross-sectional conceptual view of a semiconductor system gas sensor of another embodiment according to this invention. In FIG. 24, the gas sensor of this embodiment comprises a pair of interdigital electrodes 42 on one surface of the plate form insulation substrate 41 and N type semiconductor oxide system coated layer 43 on the electrodes, and a gas detection element with a heating membrane 44 on the other surface housed inside the tubular gas selective permeation element 2. The sensor of Embodiment 23 has the heating wire 30 arranged inside the tube, but in this embodiment, it is formed on the insulation substrate. Except that the means of heat source is different, basically others are same as those in the preceding embodiment.

(Embodiment 25)

Figure 25:
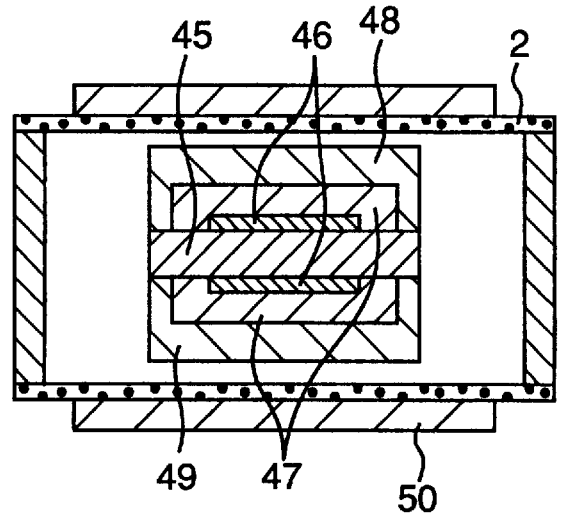
FIG. 25 is a cross-sectional view showing a gas sensor related to a 25th embodiment according to the present invention.

FIG. 25 is a cross-sectional conceptual view of a semiconductor type gas sensor of another embodiment according to this invention. In FIG. 25, the gas sensor of this embodiment comprises two pairs of interdigital electrodes 46 on both surfaces of the plate form insulation substrate 45, N type semiconductor oxide system sinter layer 47 on the electrode of each surface, and in addition, a porous carbon monoxide catalyst layer 48 on one of the N type semiconductor oxide system coated layers, and a gas detection element with porous selective hydrogen oxydation catalyst layer 49 with no carbon dioxide oxidizing capabilities but with hydrogen oxidizing capabilities mounted on the other side, wherein they are housed in a tubular ceramic gas selective permeation element with a heating means provided on the circumferential portion. Because the semiconductor system element not only detects gas but also is sensitive to characteristic changes of the environment such as temperature characteristics, this is configured to cancel effects other than carbon monoxide. The heat source for operating the gas sensor is fed by the heating means 50. Through the gas selective permeation element, the selected gas enters the element inside the tube, and on one side, carbon monoxide is removed at the porous carbon monoxide oxidation catalyst layer and reaches the semiconductor element surface, and on the other side, gas reaches the element surface with carbon monoxide kept containing but with hydrogen removed. By taking the ratio of the sensor outputs obtained from these two, various noise effects can be canceled and the gas can be detected at high accuracy. The effects, etc. related to durability of the sensor according to this embodiment are same as those described above.

(Embodiment 26)

Figure 26A:
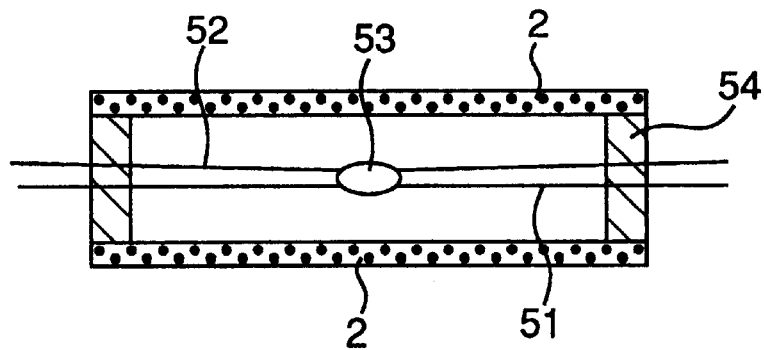
FIG. 26A is a cross-sectional view showing a gas sensor related to a 26th embodiment according to the present invention.
Figure 26B:
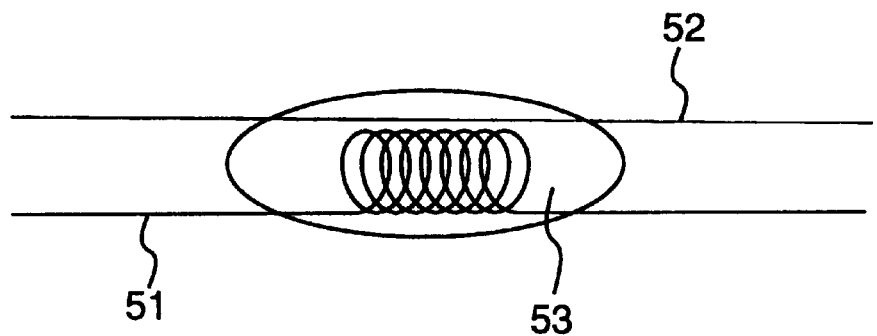
FIG. 26B is an enlarged fragmentary view of the gas sensor show in FIG. 26B.

FIG. 26A, shows a cross-sectional conceptual view of a semiconductor gas sensor of another embodiment according to this invention. In FIG. 26, FIG. 26A, the gas sensor of this embodiment houses a gas detection element configured by providing N type semiconductor oxide system coated layer 53 on the surface of the element composed with a heater coil 51 and a lead wire 52 as shown in FIG. 26B, Which is a fragmentary enlarged view, inside a tubular gas selective permeation element 2. Platinum wire coil thin wire 23 of 20 to 50 $\mu$m in diameter and platinum lead wire are arranged, and the paste containing semiconductor oxide as described before is prepared and after applying the paste in the form of spheroid shape, the platinum coil wire is energized, dried, and sintered to form the element. After housing the element fabricated in this way inside the nearly cylindrical porous body, it is sealed to fabricate a gas sensor. Since the sensor is small-size, an element with less power consumption can be fabricated. The operation of this gas sensor is to measure the change of resistance at both ends of the lead wire by energizing the platinum coil wire 23 and setting to the working temperature. The effects on durability, etc. of the sensor by the gas selective permeation element are same as those described above.

(Embodiment 27)

Figure 27:
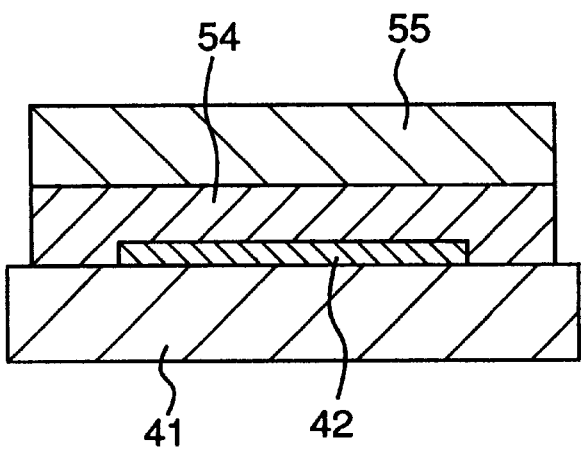
FIG. 27 is a cross-sectional view showing a gas sensor related to a 27th embodiment according to the present invention.

FIG. 27 shows a cross-sectional conceptual view of the semiconductor type gas sensor of another embodiment according to this invention. In FIG. 27, the gas sensor of this embodiment is a laminated membrane comprising the first coated layer 54 in which the N type semiconductor oxide system coated layer on the electrodes 42, contains indium oxide and the second coated layer 55 containing noble metal or P type semiconductor oxide sensitizer.

Description is made on the manufacturing method of the semiconductor system gas sensor as follows. For a method for forming interdigital electrode membrane on various shapes of substrate, dry methods such as conventionally known electron beam deposition or sputtering, plating or thick-film printing method are applicable, but the thick-film printing which provides excellent productivity and inexpensive cost is advantageous. The film may be directly printed or transferred. For a process for forming N type semiconductor coating, etc., metal oxide powders are made into paste by an automatic mortar or a disperser such as a triple roll mill together with a binding agent such as glass, high molecular additives such as carboxymethyl cellulose for adjusting paste characteristics, and solvents, and the paste is printed, dried, and sintered by the screen printing process. Of the oxides which provide various N type semiconductor characteristics, coatings of stannic oxide, indium oxide, and zinc oxide provide good gas sensitivity. Applying a thin coat of P type semiconductor oxides such as iron, manganese, copper, nickel, chromium, cobalt, etc. on the coating containing these oxides can achieve sensitivity improving effects because these oxides provide high gas adsoptivity and they possess physical sensitizing effects which change the Fermi level of N type semiconductor oxide on the lower layer in addition to chemical sensitizing effects which cause N type semiconductor oxide on the lower layer to spill over the gas. When the amount of P type material excessively increases, characteristics of N type are impaired and the characteristics to detect gas and increase the resistance are emphasized and the operation becomes unstable. Of the P type semiconductor oxides represented by various transition metal oxides, sensitization action is difficult to use if reactivity is strong, and therefore, choice of materials with propel reactivity is desirable. From this point of view, iron compounds provide proper reactivity and are suitable. For iron compounds which can be applied to this object, compounds of various forms can be mentioned. In addition to the single compound of iron, composite oxide or mixture with spinel, perovskite, and other structures can be used. For the purpose of sensitization, the same effects can be achieved by randomly dispersing P type oxide in N type semiconductor oxide coating in place of laminating both semiconductor oxides. The same sensitization effects can be achieved by using traces of noble metal in place of P type semiconductor oxides represented by transition metal oxides. For noble metal used for this purpose, from the viewpoint of carbon monoxide adsorption characteristics, platinum, palladium, rhodium are preferable. The maximum sensitivity can be obtained when the sensor working temperature ranges from 100° C. (373K) to 200° C. (473K). Below 100° C., influence of water vapor adsorption appears and over 200° C., oxidation catalyst action of carbon monoxide appears and sensitivity degrades. However, if it is used in the combustion exhaust gas passage, it is used in the temperature range from 300–400° C., though the sensitivity degrades.

The evaluation results of a trially produced sensor element according to this invention are shown as follows.

Using a 10-mm-square (1 mm thick) porous alumina substrate (pore size: about 1 $\mu$m), one surface was covered with polyvinylidene chloride film, and after hydrolyzing aluminum isopropoxide with distilled water, it was immersed for 10 seconds in a sol solution (Al concentration: 0.6 mol/L) obtained by dissolving hydrochloric acid, and after drying at room temperature for about 8 hours, operation to sinter to 773 K at 50 K/h was repeated 10 times to control pore diameter. The boehmite film has changed to $\gamma$ alumina. When it was directly confirmed with a scanning type electron microscope, the pore size was about 4 Å, In this way, a ceramic gas permselective membrane flat plate was fabricated. The tubular ceramic gas selective permeation was fabricated in the following procedure. As a support for controlling pores, a tube with pore size of 0.2 $\mu$m made of ceramics hollow thread membrane 3 mm in outside diameter, 2 mm in inside diameter, and 200 mm long (precision filtration membrane) was used, and with one end sealed, water was allowed to permeate in the pore, an then, using the aluminum based sol, continuous filtration was carried out for one hour. After drying for 8 hours at room temperature, operation for sintering to 773 K at 50 K/h was repeated 10 times to control the pore diameter. With this method, a ceramic gas selective permeation with pore diameter of about 5 Å was obtained. This tube was cut to a required length with a diamond cutter and used for a sensor. Using the 10-mm-square ceramic gas selective permeation, and to the one-half area, using hydrochloric acid solution of palladium chloride, palladium was carried by a method for reducing with sodium borohydride. Then, platinum electrodes were formed on this by patterning in the size of 3 mm square and using the electron beam deposition process. In addition, yttria stabilized zirconia membrane was formed about 5-$\mu$m thick by sputtering, and then, using the sol-gel method, alumina film was formed.

Figure 28:
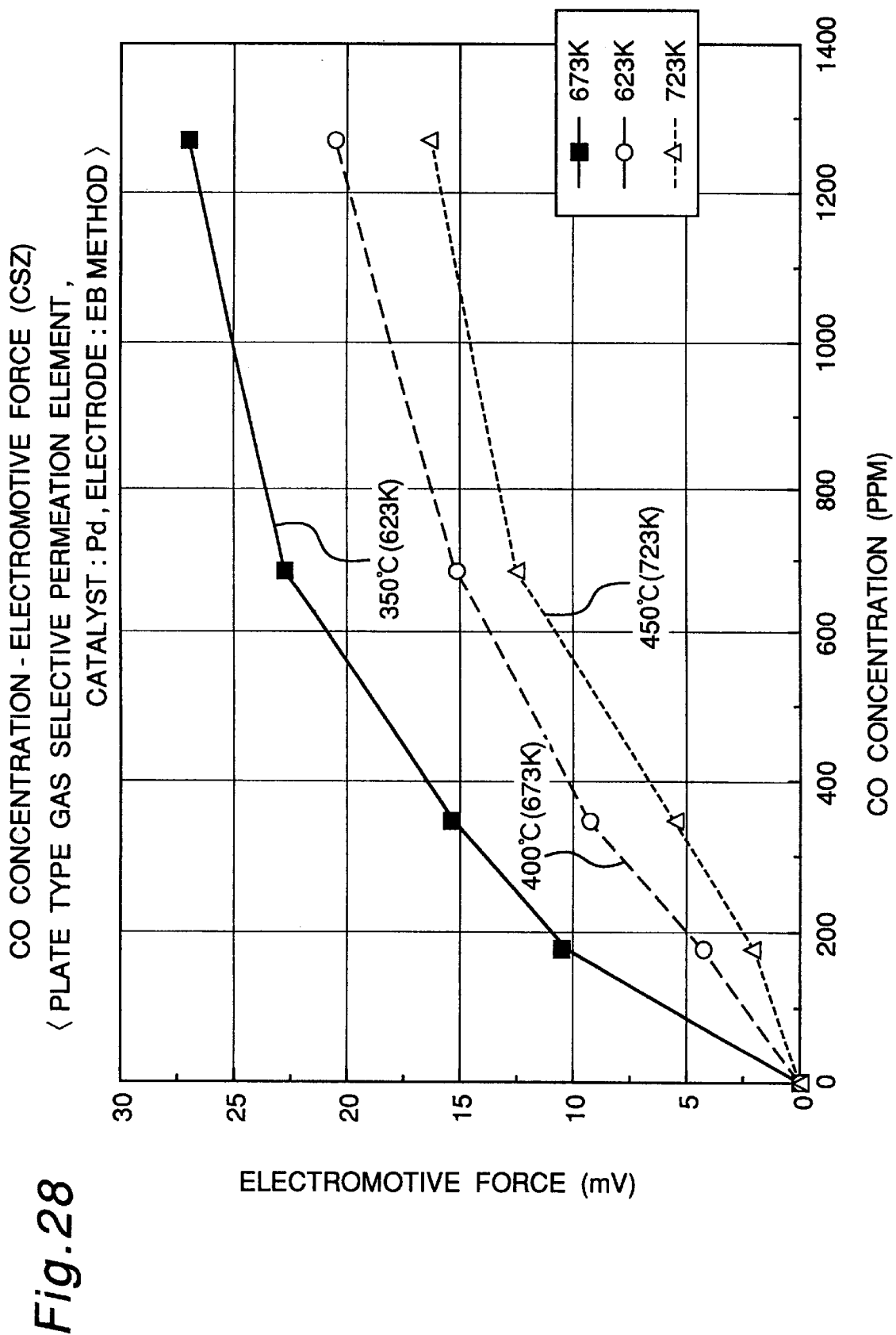
FIG. 28 is a graph showing characteristics of the gas sensor related to the first embodiment according to the present invention.
Figure 29:
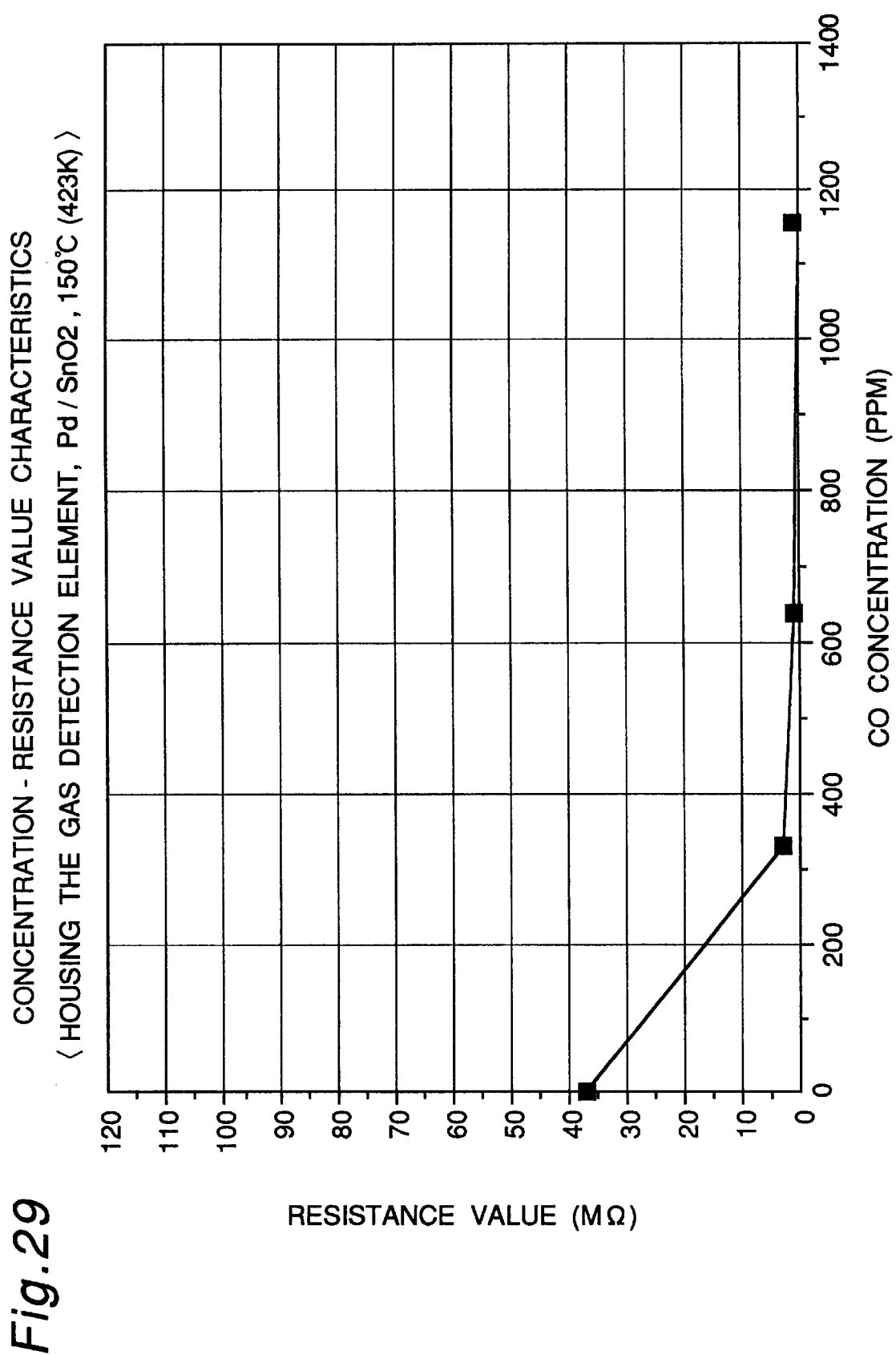
FIG. 29 is a graph showing characteristics of the gas sensor related to the second embodiment according to the present invention.
Figure 30:
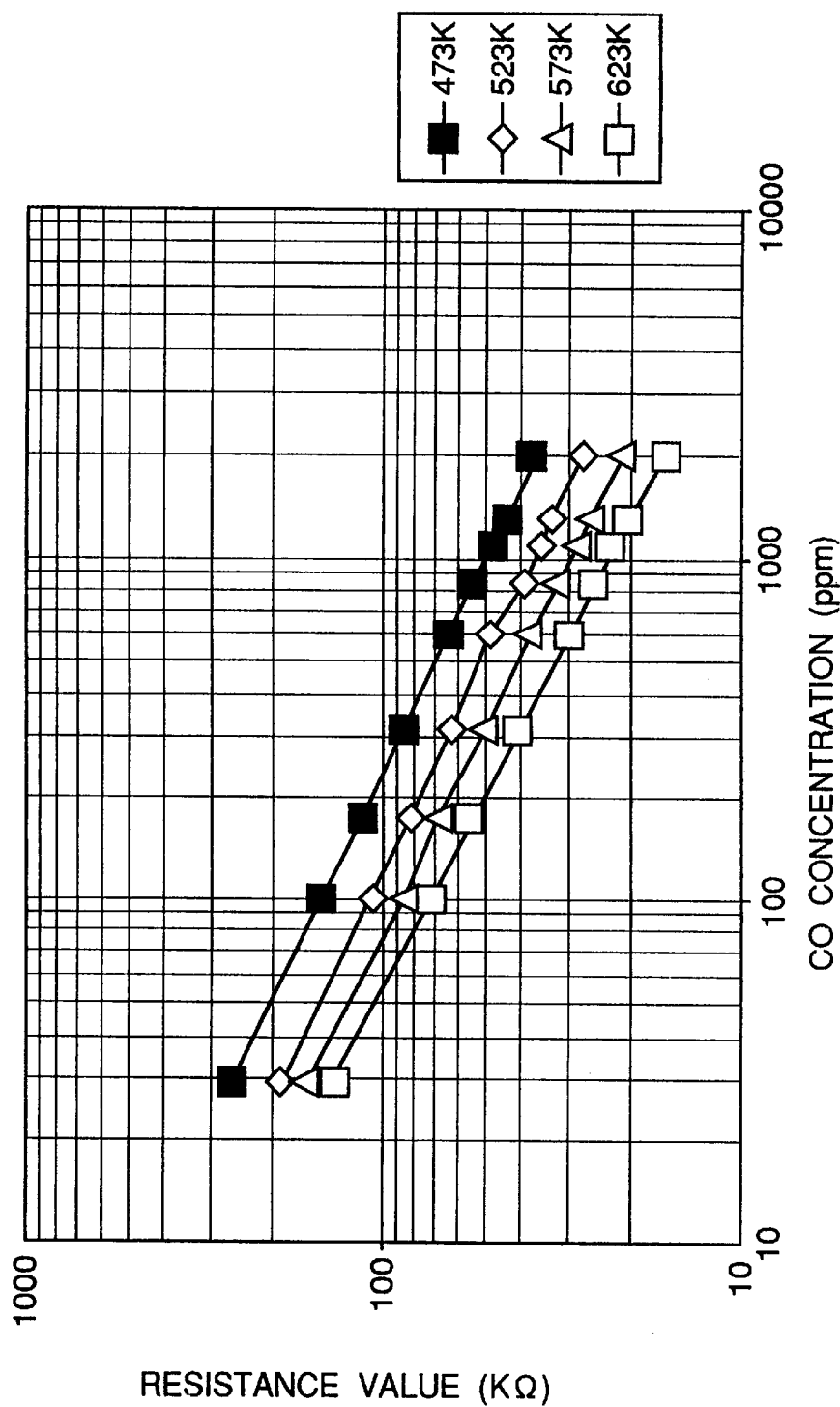
FIG. 30 is a graph showing characteristics of the gas sensor related to the third embodiment according to the present invention.

With respect to this sensor element, using a flow type performance evaluating testing equipment, air containing carbon monoxide was fed, and the relationship between the carbon monoxide concentration and electromotive force output characteristics of the sensor was evaluated, the results of which are shown in FIG. 28.

Seventy-five parts by weight of In 203, 25 parts by weight of CuFe2O4, 30 ppm of Au fine particles, 0.5 parts by weight of borosilicate glass, and 0.5 parts by weight of methyl cellulose were dispersed for preparation together with a solvent primarily comprising a terpineol and ethyl cellosolb by an automatic mortar and triple roller mill and N type semiconductor paste was prepared. On 50 μm platinum coil and 100 μm lead wire, the said paste was applied in a spheroid 0.3 mm in the maximum width and 0.5 mm long and sintered at 400° C. to fabricate two semiconductor elements. The said element C and further the element were housed in the said porous body (12 mm in size), and with the platinum lead wire taken out, both ends of the tube of the porous body were sealed with silicate-base adhesive containing filling agent (the gas sensor of this embodiment is hereinafter called the "gas sensor D"). With respect to the element C, using a flow type gas sensor characteristic evaluation testing equipment, the relationship between carbon monoxide concentration and resistance was evaluated, the results of which were shown in FIG. 29, and result of D in FIG. 30. The results of FIG. 29 and FIG. 30 indicate that housing the gas detection element inside the porous body has an effect of stabilizing temperature characteristics.

Figure 31:
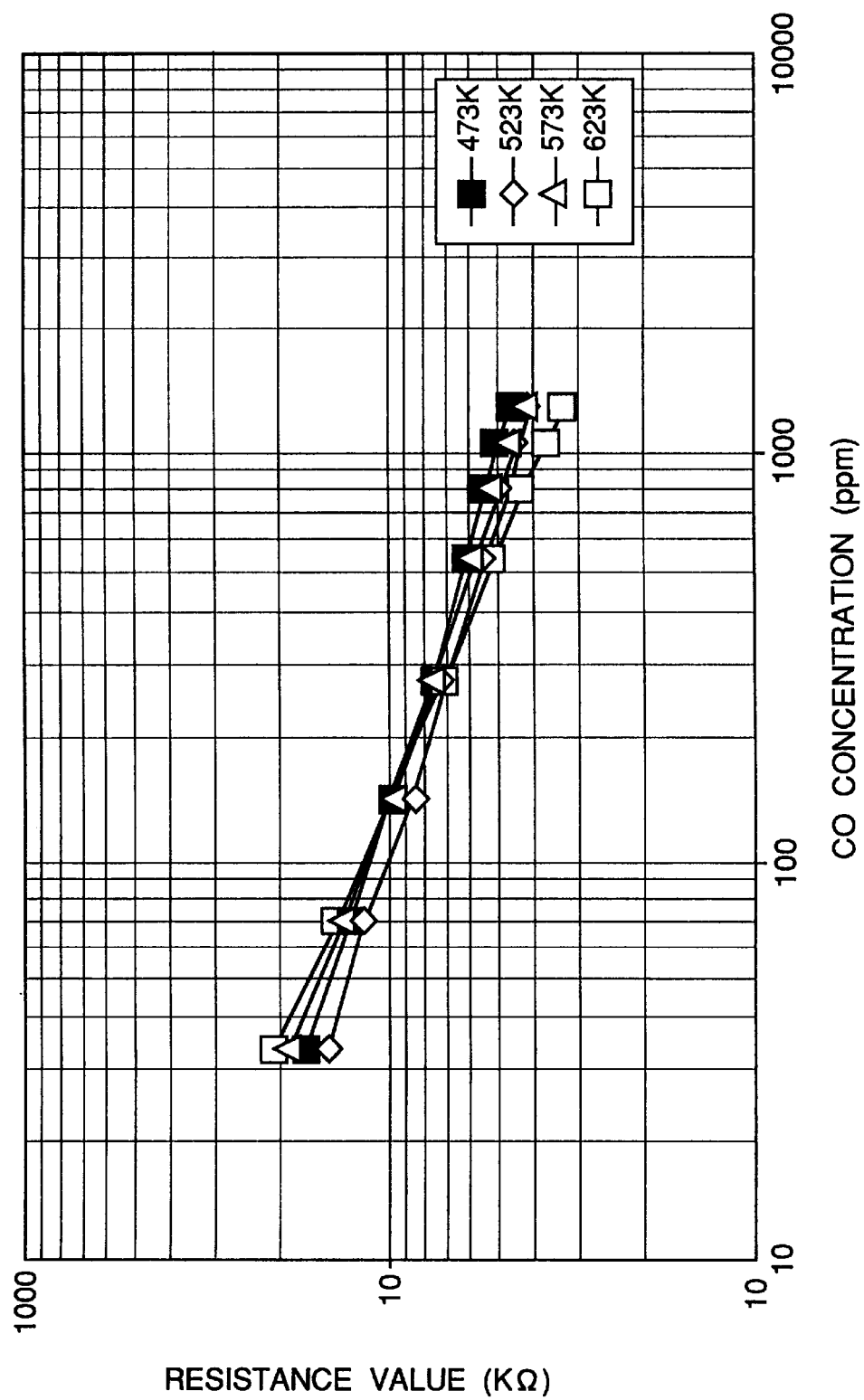
FIG. 31 is a graph showing characteristics of the gas sensor related to the fourth embodiment according to the present invention.

Using an alumina tube 1.2 mmφ in outside diameter, 0.8 mmφ in inside diameter, and 4 mm long, an interdigital electrode was formed on this surface, and to the surface, a stannic oxide sol was applied, and then, hydrochloric acid aqueous solution of palladium chloride was added to fabricate a semiconductor type gas sensor, and with a platinum lead wire taken out, it was housed in a ceramic gas selective permeation (10 mm long) with a cylindrical tip end, and both ends were sealed with silica-alumina glass to fabricate a gas sensor. This sensor was evaluated using a flow type performance evaluating testing equipment, the results of which are shown in FIG. 31. High sensitivity is obtained.

Figure 32:
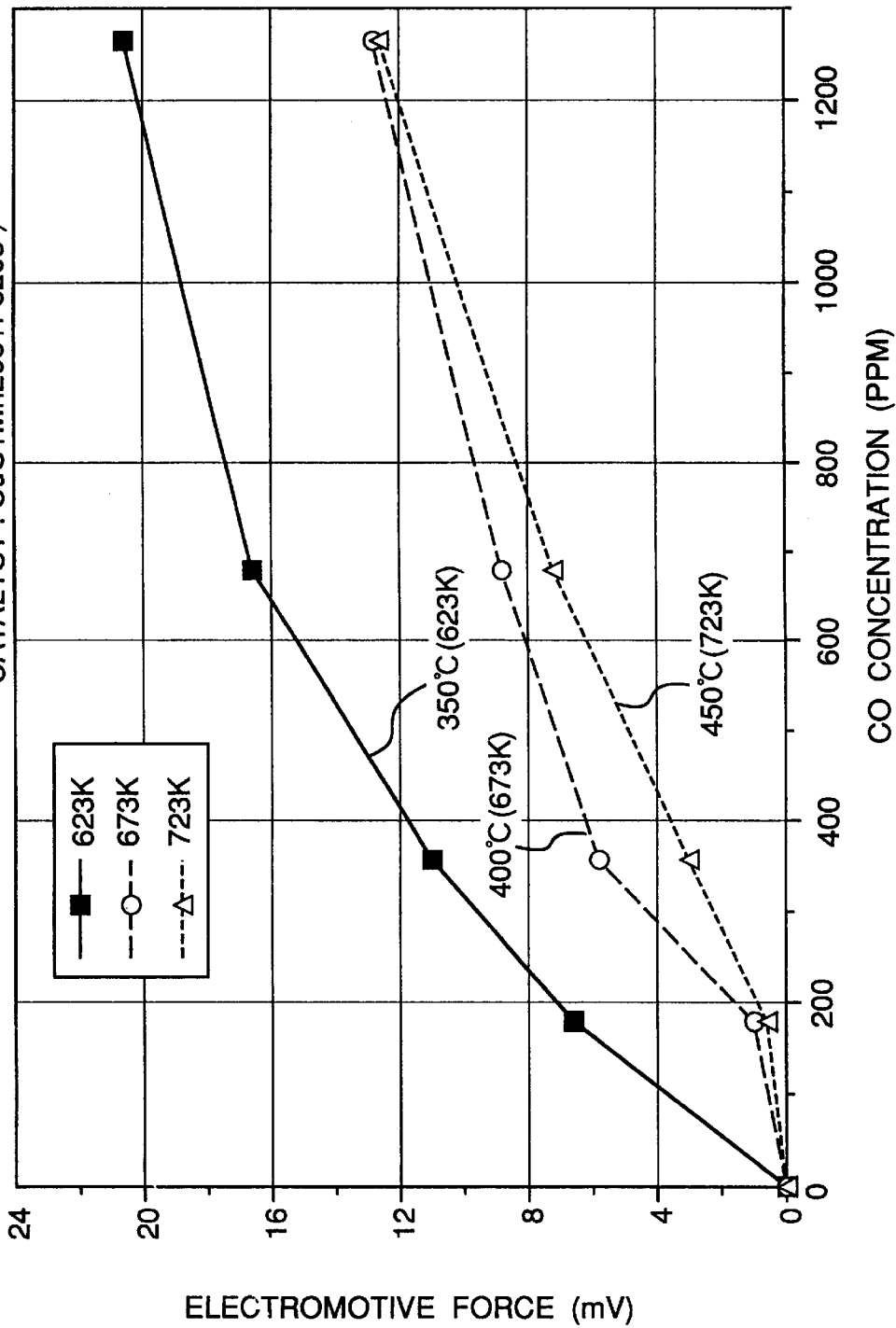
FIG. 32 is a graph showing characteristics of the gas sensor related to the fifth embodiment according to the present invention.

Using a calcia stabilized zirconia tube of 1.2 mmφ in outside diameter, 0.8 mmφ in inside diameter, and 4 mm long, on this surface, a pair of platinum electrodes 3 mm wide each were fabricated (transferring method was used), and with the platinum wire taken out, the electrode on one side is covered with composite oxide porous membrane containing manganese, copper, and iron oxide to fabricate an element, and then, it was evaluated in the same manner as in the preceding paragraph. The evaluation results are shown in FIG. 32. At 350° C., the maximum electromotive force output is obtained. As observed above, it has been confirmed that even if Knudsen diffusion pores are provided, the basic characteristics as a carbon monoxide sensor will not change.

In order to compare the technique of this invention with the conventional technique, comparison evaluating tests were carried out with respect to durability using an element housed inside the cylindrical gas selective permeation and an element not housed. The sensors were arranged in an exhaust gas passage of a gas hot-water supply apparatus, and to the exhaust gas, about 100 ppm of SO2 and 50 ppm of organic low-molecular silicone were added for the promoted acceleration test, and the change of the sensor with time was investigated. With the naked sensor corresponding to the conventional technique, in the case of semiconductor system, for about 100 hours, and in the case of solid electrolyte system, for about 600 hours, the resistance and output became less than one half and deterioration occurred, whereas with the sensor of the configuration according to this invention, even after 3000 hours passed, no changes in the characteristics were recognized and it was confirmed that the sensor is stable, and the evaluation is still continuously underway.

The gas sensor according to this invention is embodied in the forms as described above, and the following effects are obtained.

With respect to detection of carbon monoxide, the drawback of fail-out can be covered, and reliability of element configuration is high, and it is suited for installing the gas sensor to combustion equipment.

In the practical aspect of the chemical sensor, with respect to the durability which has been the biggest problem, a porous body is used for restricting interfering gas to reach the sensor element, and by housing the sensor in the porous body, acidic gas which provides poisoning effects on the gas sensor can be completely blocked; thereby remarkably extended life can be expected, and a gas sensor system with extremely high reliability can be built.

Action in the diffusion controlling area where temperature characteristics are markedly stabilized is enabled, and unstability of the gas sensor, which has been the serious problem of the gas sensor, can be solved.

What is claimed is:

1. A carbon monoxide gas sensor comprising:

a base material forming a closed space;

a gas detection element disposed in the closed space formed by said base material; and a heating device for heating said gas detection element, wherein at least a portion of said base material includes a gas selective permeation element provided with a plurality of pores, wherein each of said Pores is provided with a coating membrane so that the average pore diameter size is 3–100 Å in order to prevent gases, other than carbon monoxide, from passing through said pores, wherein said gas detection element comes into contact with gases containing a gas to be detected via said gas selective permeation element, and wherein a surface of said gas selective permeation element is coated with zirconia, silica, or a mixture thereof.

2. A carbon monoxide gas sensor comprising:

a gas detection element;

a gas selective permeation element which covers at least a part of said gas detection element, said gas selective permeation element being in close contact with said gas detection element such that gases containing a gas to be detected come into contact with said gas detection element via said gas selective permeation element; and a heating means for heating said gas detection element, wherein said gas selective permeation element is provided with a plurality of pores, each of said pores having a coating membrane so that the average pore diameter size is 3–100 Å in order to prevent gases, other than carbon monoxide, from permeating said gas selective permeation element, wherein a surface of said gas selective permeation element is coated with zirconia, silica, or a mixture thereof.

3. A carbon monoxide gas sensor comprising:

a first gas selective permeation element;

a first electrode membrane laminated on a side of said first gas selective permeation element;

an oxygen ion conductive solid electrolyte membrane laminated on said first electrode membrane;

a second electrode membrane laminated on said oxygen ion conductive solid electrolyte membrane;

a second gas selective permeation element laminated on said second electrode membrane;

an oxidation catalyst provided on one of said first and second gas selective permeation elements; and a heating membrane laminated on the other of said first and second gas selective permeation elements, wherein each of said first and second gas selective permeation elements is provided with a plurality of pores, and wherein each of said pores is provided with a coating membrane so that the average pore diameter size is 3–100 Å in order to prevent gases, other than carbon monoxide, from permeating said gas selective permeation elements.

4. A carbon monoxide gas sensor comprising:

a gas selective permeation element provided with a plurality of pores, each of said pores having a coating membrane so that the average pore diameter size is 3–100 Å in order to prevent gases, other than carbon monoxide, from permeating said gas selective permeation element;

a pair of electrodes formed on a surface of said gas selective permeation element;

a ceramic insulator layer covering said pair of electrodes; and a heating membrane layer formed on said ceramic insulator layer, wherein a first section of said gas selective permeation element is provided with an oxidation catalyst inside the pores thereof, and one of said electrodes is positioned on said first section of said gas selective permeation element.

5. A carbon monoxide gas sensor comprising:

a pair of plate-form gas selective permeation elements provided with a plurality of pores, each of said pores having a coating membrane so that the average pore diameter size is 3–100 Å in order to prevent gases, other than carbon monoxide, from permeating said permeation elements, a heating membrane positioned on a first side of one of said gas selective permeation elements;

a first electrode membrane formed on a second side of said one gas selective permeation element;

an oxygen ion conductive solid electrolyte membrane laminated on said first electrode membrane and said one gas selective permeation element;

a second electrode membrane laminated on said oxygen ion conductive solid electrolyte membrane; and a porous catalyst membrane laminated on said second electrode membrane and said oxygen ion conductive solid electrolyte membrane, wherein the other gas selective permeation element is provided on said porous catalyst membrane.

6. A carbon monoxide gas sensor comprising:

a ceramic insulator plate;

an oxygen ion conductive solid electrolyte membrane provided on a first surface of said ceramic insulator plate;

a pair of electrodes provided on a surface of said oxygen ion conductive solid electrolyte membrane;

a porous catalyst membrane layer positioned on one of said electrodes;

a plate-shaped gas selective permeation element positioned over said porous catalyst membrane layer; and a heating membrane formed on a surface of said plate-shaped gas selective permeation element, wherein said oxygen ion conductive solid electrolyte membrane, said electrodes, and said porous catalyst membrane layer are sealed between said plate-shaped gas selective permeation element and said ceramic insulator plate, and wherein said plate-shaped gas selective permeation element is provided with a plurality of pores having an average pore diameter of 3–100 Å for preventing gases, other than carbon monoxide, from permeating said gas selective permeation element.

7. A carbon monoxide gas sensor comprising:

a tubular gas selective permeation element forming a closed interior space;

a gas detection element housed in said closed interior space;

a heating means arranged in said closed interior space or at an outside surface of said tubular gas selective permeation element;

wherein said tubular gas selective permeation element is provided with a plurality of pores, each of said pores having a coating membrane so that the average pore diameter size is 3–100 Å in order to prevent gases, other than carbon monoxide, from permeating said tubular gas selective permeation element.

8. A carbon monoxide gas sensor as claimed in claim 7, wherein said gas detection element comprises:

an oxygen ion conductor;

a pair of electrode membranes provided on opposite surfaces of said oxygen ion conductor; and a porous oxidation catalyst layer provided on one of said electrode membranes, wherein said heating means is provided on a circumferential portion of said tubular gas selective permeation element.

9. A carbon monoxide gas sensor as claimed in claim 8, wherein said porous oxidation catalyst layer is formed of ceramic paper comprising oxidation catalyst particles mixed in ceramic fiber.

10. A carbon monoxide gas sensor as claimed in claim 8, further comprising a porous layer formed on said electrode membrane which does not include said porous oxidation catalyst layer.

11. A carbon monoxide gas sensor as claimed in claim 7, wherein said gas detection element comprises:

a plate-shaped oxygen ion conductor;

a pair of electrode membranes provided on one side of said plate-shaped oxygen ion conductor; and a porous oxidation catalyst layer provided on one of said electrode membranes, wherein said heating means is provided on a circumferential portion of said tubular gas selective permeation element.

12. A carbon monoxide gas sensor as claimed in claim 11, wherein ceramic paper comprising oxidation catalyst particles mixed in ceramic fiber is used for said porous oxidation catalyst layer.

13. A carbon monoxide gas sensor as claimed in claim 11, further comprising a porous layer formed on said electrode membrane which does not include said porous oxidation catalyst layer.

14. A carbon monoxide gas sensor as claimed in claim 7, where in said gas detection element comprises:

a plate-shaped oxygen ion conductor having a first side and a second side;

a pair of electrode membranes disposed on the first side of said plate-shaped oxygen ion conductor; and an insulator plate disposed on the second side of said plate-shaped oxygen ion conductor, wherein said heating means comprises a heating membrane arranged on said insulator plate.

15. A carbon monoxide gas sensor as claimed in claim 14, wherein said porous oxidation catalyst layer includes ceramic paper comprising oxidation catalyst particles mixed in ceramic fiber.

16. A carbon monoxide gas sensor as claimed in claim 14, further comprising a porous layer formed on said electrode membrane which does not include said porous oxidation catalyst layer.

17. A carbon monoxide sensor as claimed in claim 7, wherein said gas detection element comprises:

- a tubular oxygen ion conductor having an inner surface and an outer surface;
- a pair of electrode membranes provided on the outer surface of said tubular oxygen ion conductor;
- a porous oxidation catalyst layer provided on one of said electrode membranes, wherein said heating means comprises a heater wire disposed inside of said tubular oxygen ion conductor.

18. A carbon monoxide gas sensor as claimed in claim 17, wherein said porous oxidation catalyst layer includes ceramic paper comprising oxidation catalyst particles mixed in ceramic fiber.

19. A carbon monoxide gas sensor as claimed in claim 17, further comprising a porous layer formed on said electrode membrane which does not include said porous oxidation catalyst layer.

20. A carbon monoxide gas sensor as claimed in claim 17, wherein said gas detection element comprises:

- a tubular insulating substrate having an inner surface and an outer surface;
- a pair of interdigital electrode membranes formed on the outer surface of said tubular insulating substrate; and
- an N-type semiconductor oxide base coated layer laminated on said electrode membranes, wherein said heater means includes a heater wire positioned inside of said tubular insulating substrate.

21. A carbon monoxide gas sensor as claimed in claim 20, wherein said N-type semiconductor oxide base coated layer is a laminated membrane comprising a first coated layer containing indium oxide and a second coated layer containing noble metal or P-type semiconductor oxide sensitizer.

22. A carbon monoxide gas sensor as claimed in claim 20, wherein said N-type semiconductor oxide base coated layer is a laminated membrane comprising a first coated layer containing stannic oxide and a second coated layer containing noble metal or a P-type semiconductor oxide sensitizer.

23. A carbon monoxide gas sensor as claimed in claim 7, wherein said gas detection element comprises:

- a plate-shaped insulating substrate having a first side and a second side;
- a pair of interdigital electrodes formed on the first side of said plate-shaped insulating substrate; and
- an N-type semiconductor oxide base coated layer laminated on said electrodes, wherein said heating means comprises a heater membrane provided on the second side of said plate-shaped insulating substrate.

24. A carbon monoxide gas sensor as claimed in claim 23, wherein said N-type semiconductor oxide base coated layer is a laminated membrane comprising a first coated layer containing indium oxide and a second coated layer containing noble metal or P-type semiconductor oxide sensitizer.

25. A carbon monoxide gas sensor as claimed in claim 23, wherein said N-type semiconductor oxide base coated layer is a laminated membrane comprising a first coated layer containing stannic oxide and a second coated layer containing noble metal or P-type semiconductor oxide sensitizer.

26. A carbon monoxide gas sensor according to claim 7, wherein said heating means is provided on an outer circumferential portion of said tubular gas selective permeation element, and said gas detection element comprises:

- a plate-shaped insulating substrate;
- two pairs of interdigital electrodes formed on opposite surfaces of said plate-shaped insulating substrate;
- an N-type semiconductor oxide base coated layer provided on each pair of interdigital electrodes;
- a porous carbon monoxide catalyst layer provided on one of said N-type semiconductor oxide base coated layers; and
- a porous selective hydrogen oxidizing catalyst layer provided on the other of said N-type semiconductor oxide base coated layers, said porous selective hydrogen oxidizing catalyst layer having hydrogen oxidizing capabilities but no carbon monoxide oxidizing capabilities.

27. A carbon monoxide gas sensor as claimed in claim 26, wherein said N-type semiconductor oxide base coated layer is a laminated membrane comprising a first coated layer containing indium oxide and a second coated layer containing noble metal or P-type semiconductor oxide sensitizer.

28. A carbon monoxide gas sensor as claimed in claim 26, wherein said N-type semiconductor oxide base coated layer is a laminated membrane comprising a first coated layer containing stannic oxide and a second coated layer containing noble metal or P-type semiconductor oxide sensitizer.

29. A carbon monoxide gas sensor as claimed in claim 7, wherein said gas detection element comprises an element including a heater coil and a lead wire, and an N-type semiconductor oxide base coated layer on the surface of the element including the heater coil and the lead wire.

30. A carbon monoxide gas sensor as claimed in claim 29, wherein said N-type semiconductor oxide base coated layer is a coated layer containing indium oxide and $CuFe_2O_4$ and gold.

31. A carbon monoxide gas sensor as claimed in claim 29, wherein said N-type semiconductor oxide base coated layer is a laminated membrane comprising a first coated layer containing indium oxide and a second coated layer containing noble metal or P-type semiconductor oxide sensitizer.

32. A carbon monoxide gas sensor as claimed in claim 29, wherein said N-type semiconductor oxide base coated layer is a laminated membrane comprising a first coated layer containing stannic oxide and a second coated layer containing noble metal or P-type semiconductor oxide sensitizer.

* * * * *